(12) United States Patent
Wilson et al.

(10) Patent No.: US 10,258,227 B1
(45) Date of Patent: Apr. 16, 2019

(54) BILATERAL ILLUMINATION ATTACHMENT FOR DENTAL CAMERA

(71) Applicant: Digital Doc LLC, El Dorado Hills, CA (US)

(72) Inventors: David D. Wilson, El Dorado Hills, CA (US); John W. Sellers, El Dorado Hills, CA (US)

(73) Assignee: Digital Doc LLC, El Dorado Hills, CA (US)

( * ) Notice: Subject to any disclaimer, the term of this patent is extended or adjusted under 35 U.S.C. 154(b) by 0 days.

(21) Appl. No.: 15/786,905

(22) Filed: Oct. 18, 2017

(51) Int. Cl.
| | |
|---|---|
| *A61B 1/06* | (2006.01) |
| *A61B 1/24* | (2006.01) |
| *A61B 1/00* | (2006.01) |
| *G03B 15/14* | (2006.01) |

(52) U.S. Cl.
CPC .................. *A61B 1/06* (2013.01); *A61B 1/24* (2013.01); *A61B 1/00096* (2013.01); *G03B 15/14* (2013.01)

(58) Field of Classification Search
CPC ......... A61B 1/06; A61B 1/24; A61B 1/00096; G03B 15/14
USPC .......................................................... 433/29
See application file for complete search history.

(56) References Cited

U.S. PATENT DOCUMENTS

| | | | | |
|---|---|---|---|---|
| 5,115,307 A * | 5/1992 | Cooper | .............. | A61B 1/00091 |
| | | | | 348/66 |
| 7,717,709 B2 * | 5/2010 | Kobayashi | ........... | A61B 1/0008 |
| | | | | 433/29 |
| 2005/0200707 A1 * | 9/2005 | Yogesan | ............ | A61B 1/00105 |
| | | | | 348/207.99 |
| 2012/0122051 A1 * | 5/2012 | Hackel | ............... | A61B 1/00096 |
| | | | | 433/29 |
| 2012/0122053 A1 * | 5/2012 | Hackel | ............... | A61B 1/00096 |
| | | | | 433/29 |
| 2013/0034826 A1 * | 2/2013 | Walsh | .................... | A61B 1/043 |
| | | | | 433/29 |
| 2013/0158350 A1 * | 6/2013 | Juergens | ............ | A61B 1/00112 |
| | | | | 600/109 |
| 2014/0377716 A1 * | 12/2014 | Rauscher | ............. | A61B 5/0088 |
| | | | | 433/29 |
| 2015/0079535 A1 * | 3/2015 | Hollenbeck | ........ | A61B 1/00096 |
| | | | | 433/29 |
| 2017/0215997 A1 * | 8/2017 | Martin | ............... | A61B 1/00013 |

* cited by examiner

*Primary Examiner* — Matthew Nelson
(74) *Attorney, Agent, or Firm* — Craig A. Simmermon

(57) ABSTRACT

Bilateral illumination attachment for dental camera is a light source that is reversibly attachable to any dental camera. Bilateral illumination attachment for dental camera has two light sources that directly face each other. When properly attached to a dental camera, bilateral illumination attachment for dental camera effectuates sub-enamel illumination or bilateral illumination of a tooth, so that the dental camera may capture a photo or image of the illuminated tooth. Bilateral illumination attachment for dental camera has a specially shaped rigid body that makes a slip-fit, press-fit, or snap-fit with the exterior surface of any dental camera. The distal end of specially shaped rigid body is sterilizeable. Bilateral illumination attachment for dental camera has a plurality of replaceable tooth cups where each tooth cup contains the two light sources. Replaceable tooth cups are placed on the tooth to effectuate sub-enamel illumination or bilateral illumination. Replaceable tooth cups are sterilizeable.

6 Claims, 18 Drawing Sheets

BILATERAL ILLUMINATION ATTACHMENT FOR DENTAL CAMERA

BACKGROUND OF THE INVENTION

1. Field of the Invention

This invention relates to sub-enamel illumination or bilateral illumination of a tooth. Sub-enamel illumination or bilateral illumination is the process of projecting light into the interior of the tooth from both the buccal side of the tooth and the lingual side of the tooth where this light is scattered in the interior of the tooth to exit the tooth from the coronal surface. An image is then taken or recorded from the scattered light emerging from the coronal surface of the tooth where this image is to help determine and categorize any impurities that might be present in the tooth such as fractures, leaking amalgam, decay, and the like. Specifically, this invention is an illumination attachment that is reversibly attachable to any dental camera. The illumination attachment functions to project light into the buccal side of the tooth and the lingual side of the tooth. The dental camera functions to capture the image of the scattered light emerging from the coronal surface of the tooth. The dental camera is not a portion of this invention.

2. Description of Related Art

There are stand-alone devices in the prior art that effectuate sub-enamel illumination or bilateral illumination of a tooth and record an image of sub-enamel illumination or bilateral illumination of the tooth. However, there are no lighting devices that are reversibly attachable to an existing dental camera in order to effectuate sub-enamel illumination or bilateral illumination of a tooth so that the existing dental camera may capture an image of sub-enamel illumination or bilateral illumination of the tooth.

BRIEF SUMMARY OF THE INVENTION

It is an aspect of bilateral illumination attachment for dental camera to be reversibly attachable to any dental camera.

It is an aspect of bilateral illumination attachment for dental camera to effectuate sub-enamel illumination or bilateral illumination of a tooth.

It is an aspect of bilateral illumination attachment for dental camera to be sterilizeable.

It is an aspect of bilateral illumination attachment for dental camera to include a motherboard and a battery.

It is an aspect of bilateral illumination attachment for dental camera to include a dual light tooth cup.

It is an aspect of bilateral illumination attachment for dental camera to be reversibly attachable to a plurality dual light tooth cups.

A plurality of dual light tooth cups are reversibly attachable to bilateral illumination attachment for dental camera.

It is an aspect of each dual light tooth cup to include a first light source and a second light source.

It is an aspect of each dual light tooth cup to include a circuit board.

It is an aspect of each dual light tooth cup to be sterilizeable.

It is an aspect of dual light tooth cup to be reversibly slideably attachable to a rigid body of bilateral illumination attachment for dental camera.

It is an aspect of dual light tooth cup to be reversibly slideably attachable to a tooth cup slide ledge on bilateral illumination attachment for dental camera.

Figure 1:
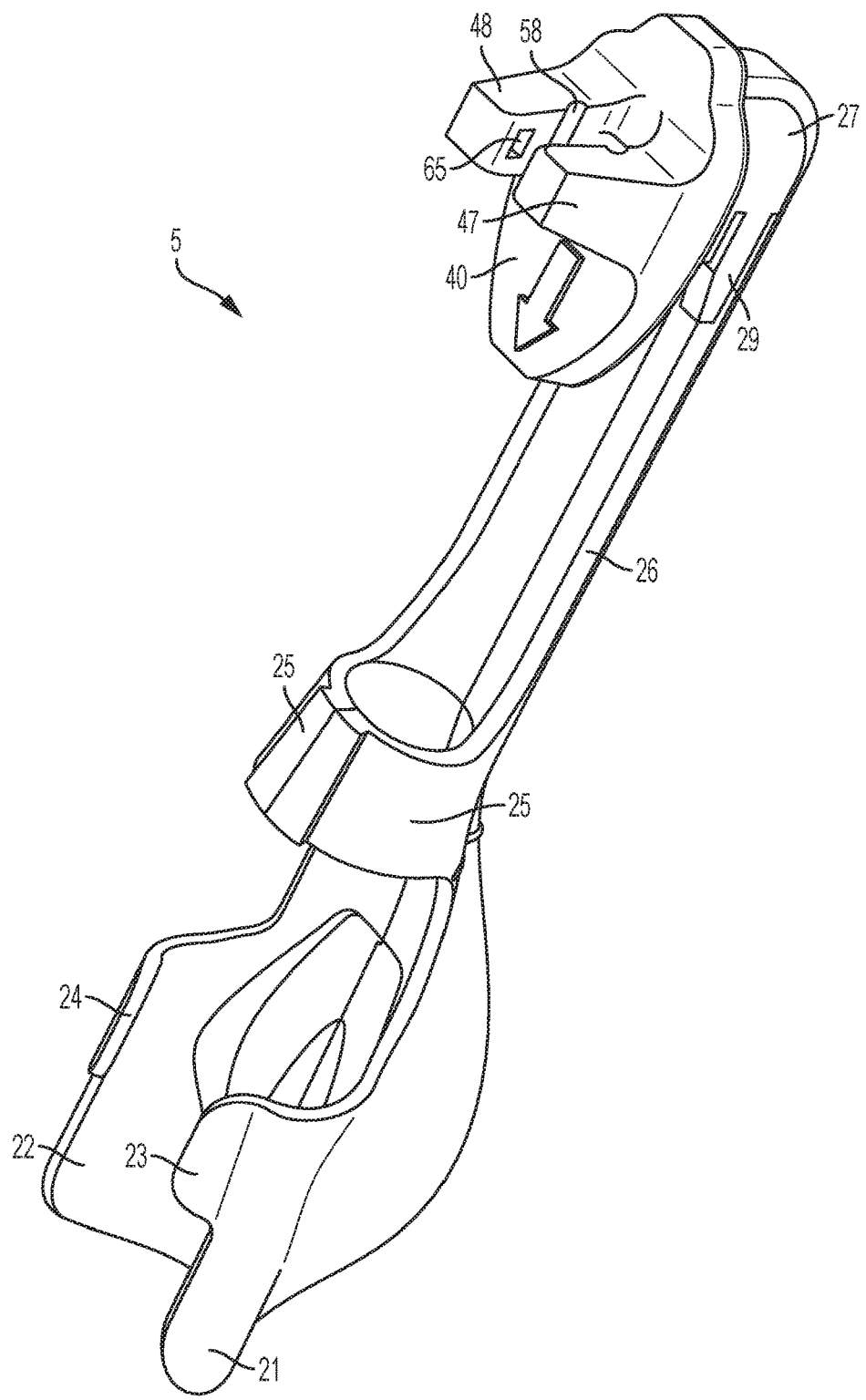
FIG. 1 is a front perspective view of bilateral illumination attachment for dental camera.
Figure 2:
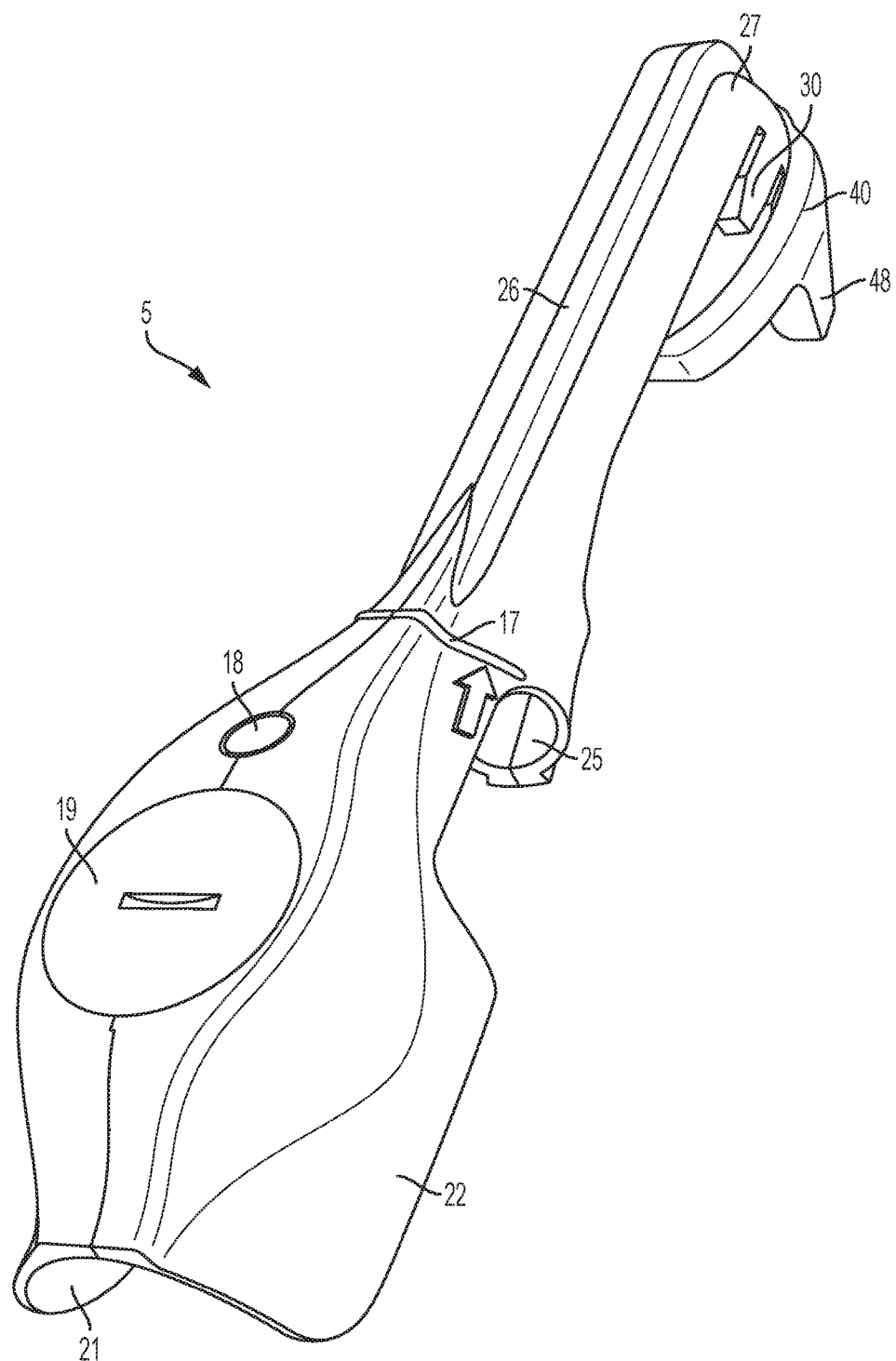
FIG. 2 is a rear perspective view of bilateral illumination attachment for dental camera.
Figure 3:
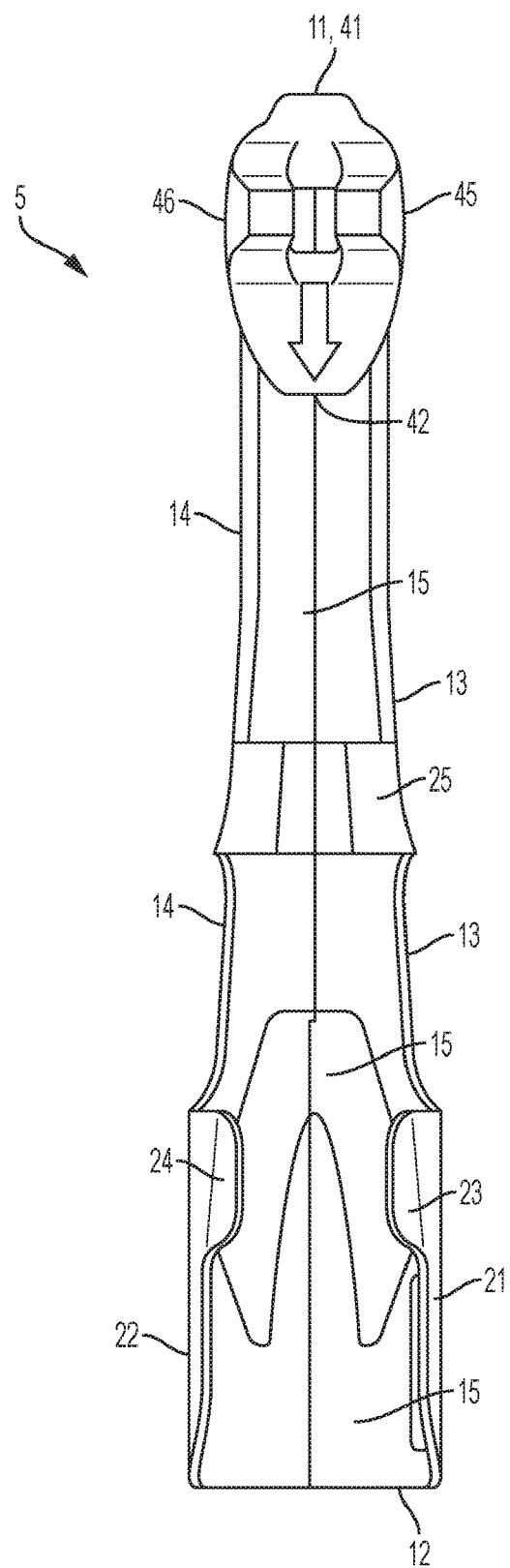
FIG. 3 is a front elevation view of bilateral illumination attachment for dental camera.
Figure 4:
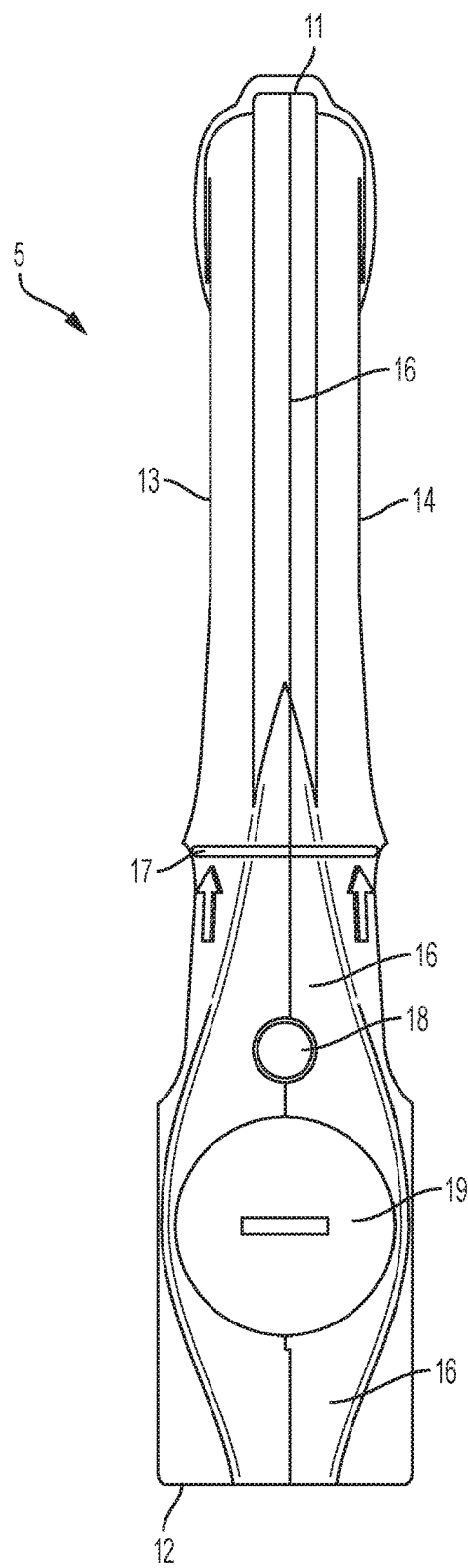
FIG. 4 is a rear elevation view of bilateral illumination attachment for dental camera.
Figure 5:
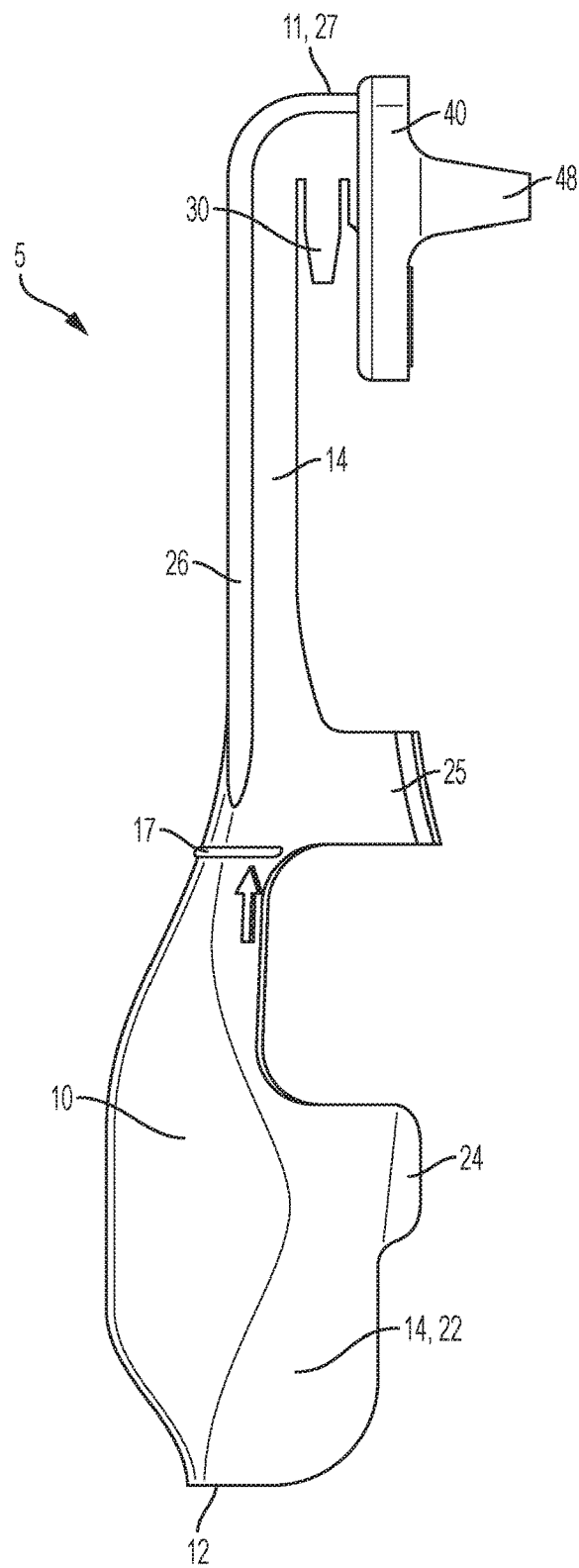
FIG. 5 is a right side elevation view of bilateral illumination attachment for dental camera.
Figure 6:
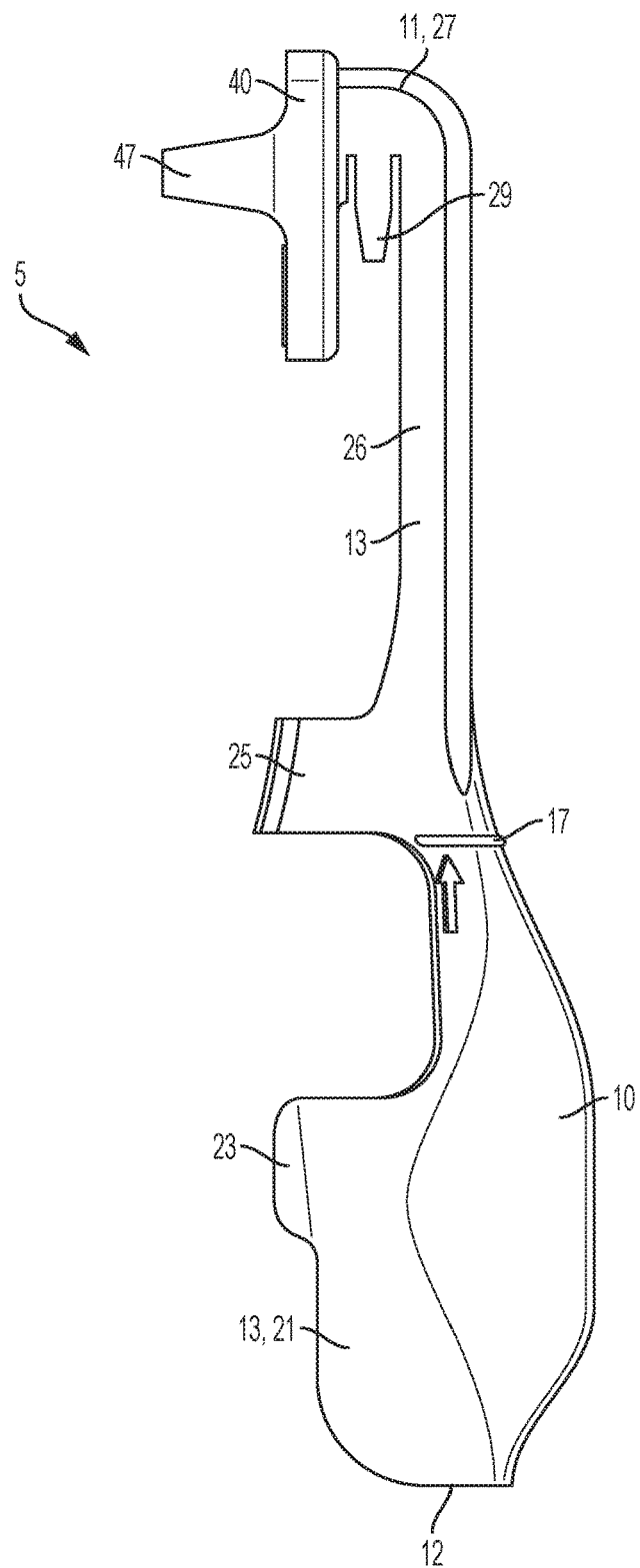
FIG. 6 is a left side elevation view of bilateral illumination attachment for dental camera.
Figure 7:
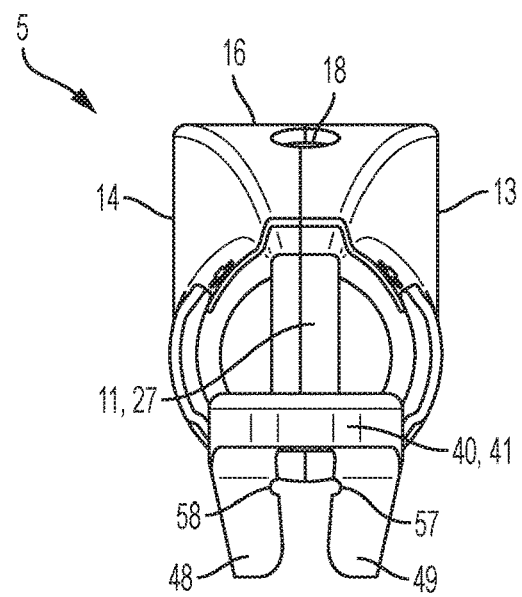
FIG. 7 is a top plan view of bilateral illumination attachment for dental camera.
Figure 8:
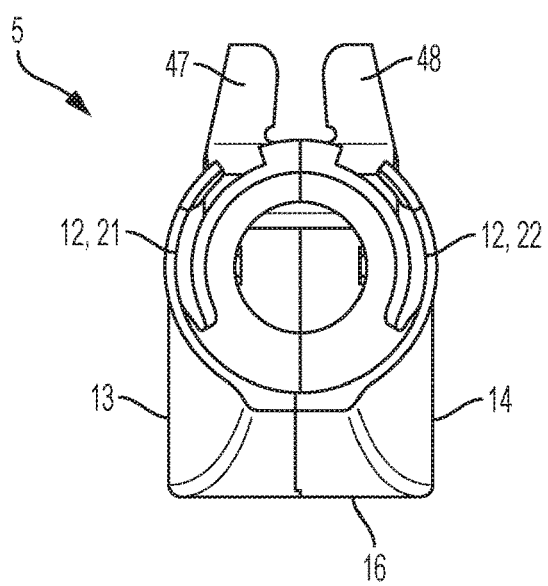
FIG. 8 is a bottom plan view of bilateral illumination attachment for dental camera.
Figure 9:
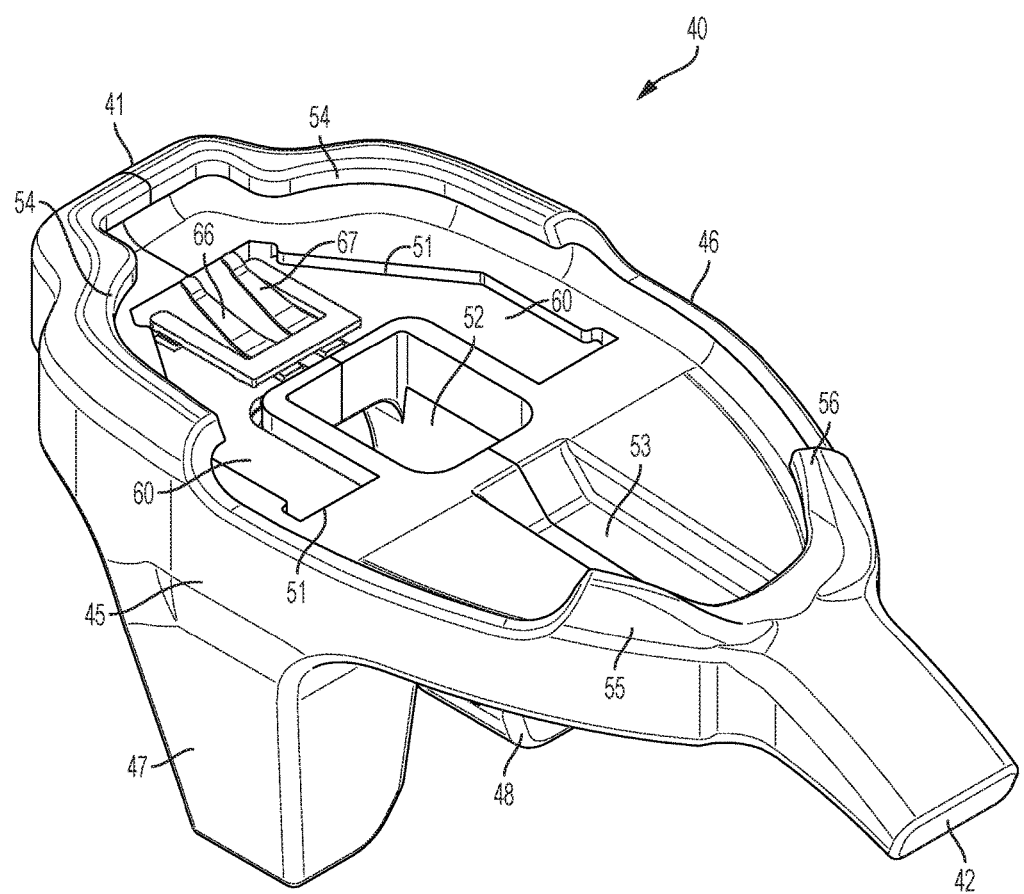
FIG. 9 is a rear perspective view of dual light tooth cup with tooth cup circuit board.
Figure 10:
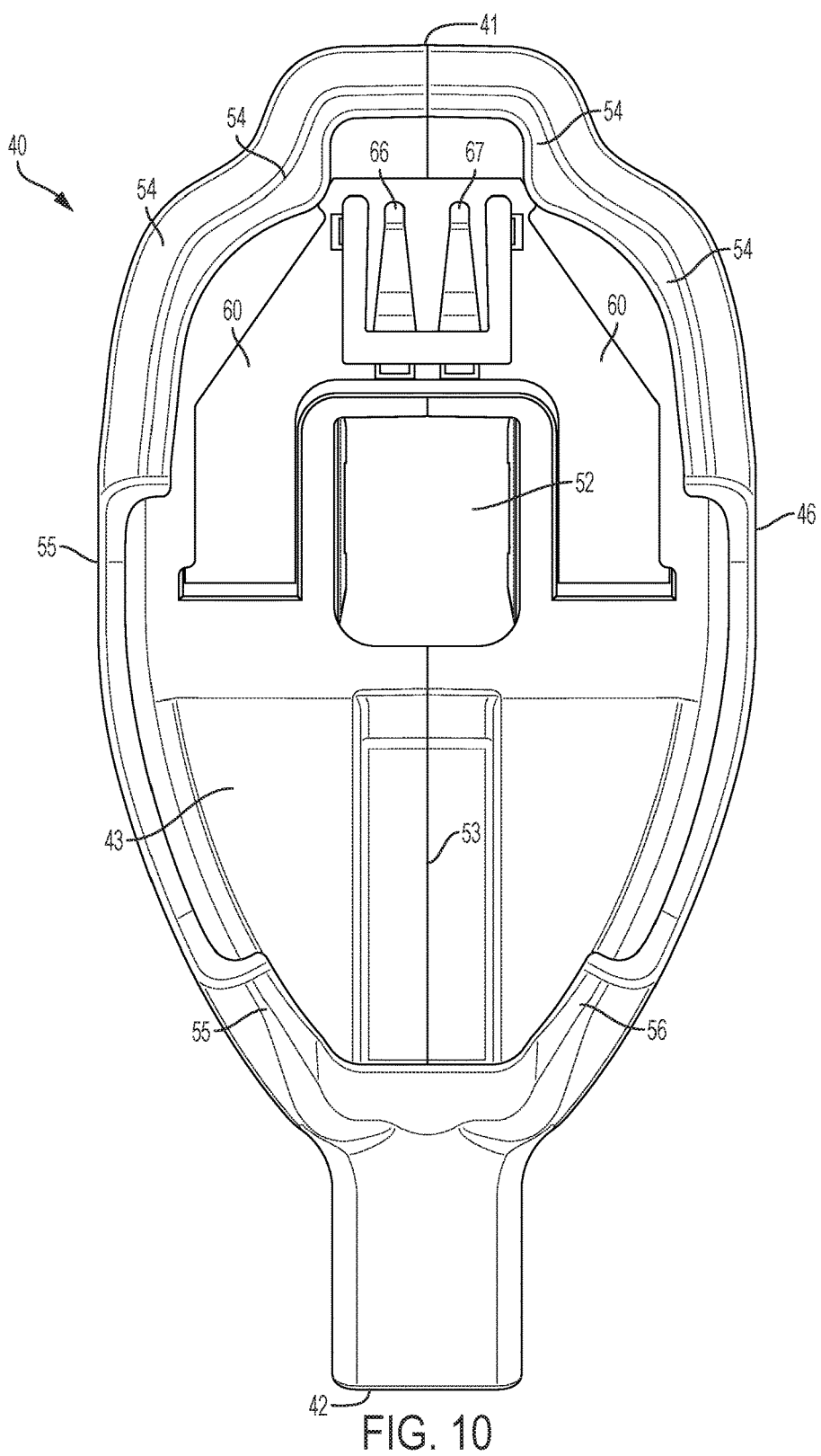
FIG. 10 is a rear elevation view of dual light tooth cup with tooth cup circuit board.
Figure 11:
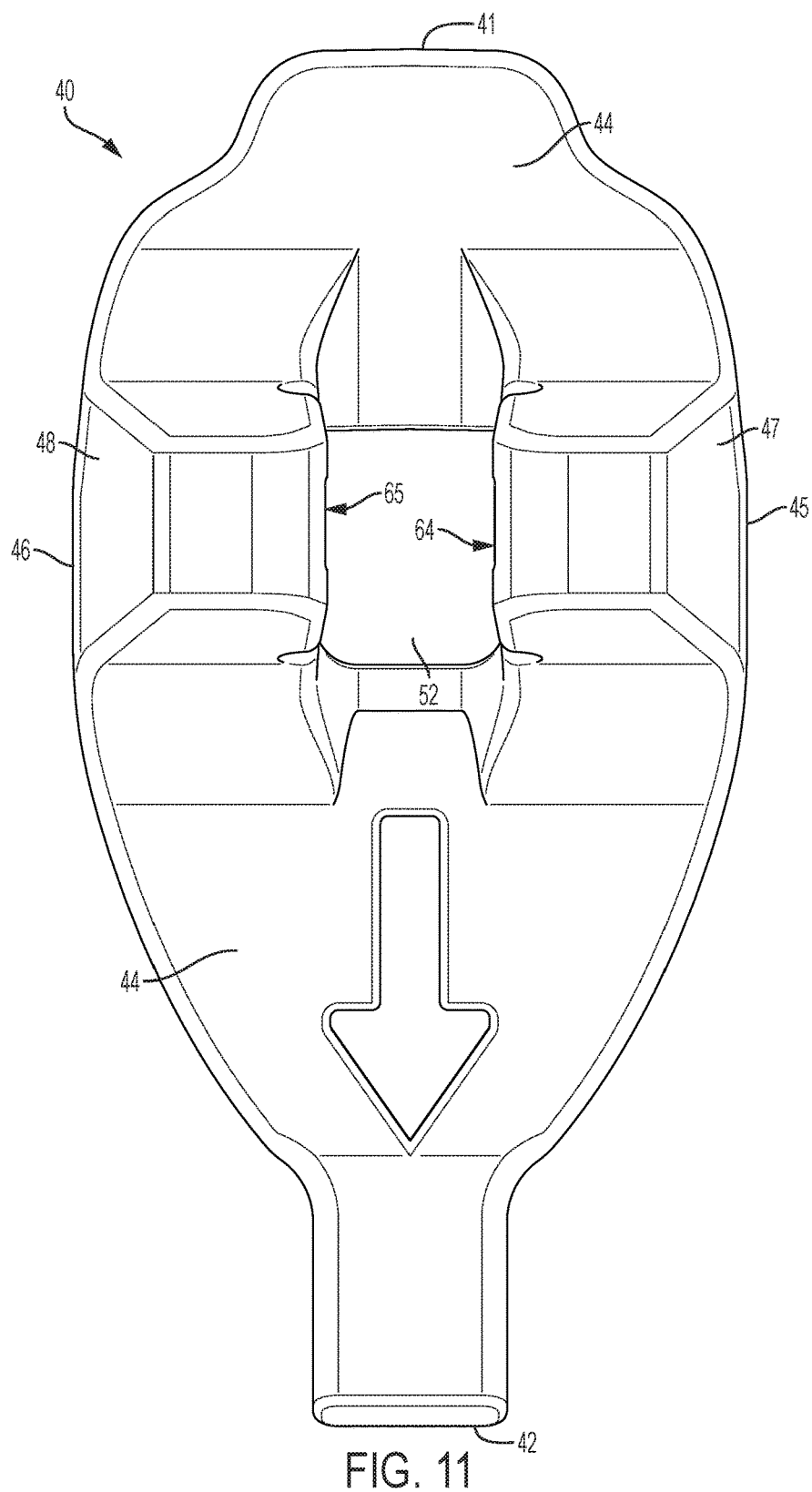
FIG. 11 is a front elevation view of dual light tooth cup with tooth cup circuit board.
Figure 12:
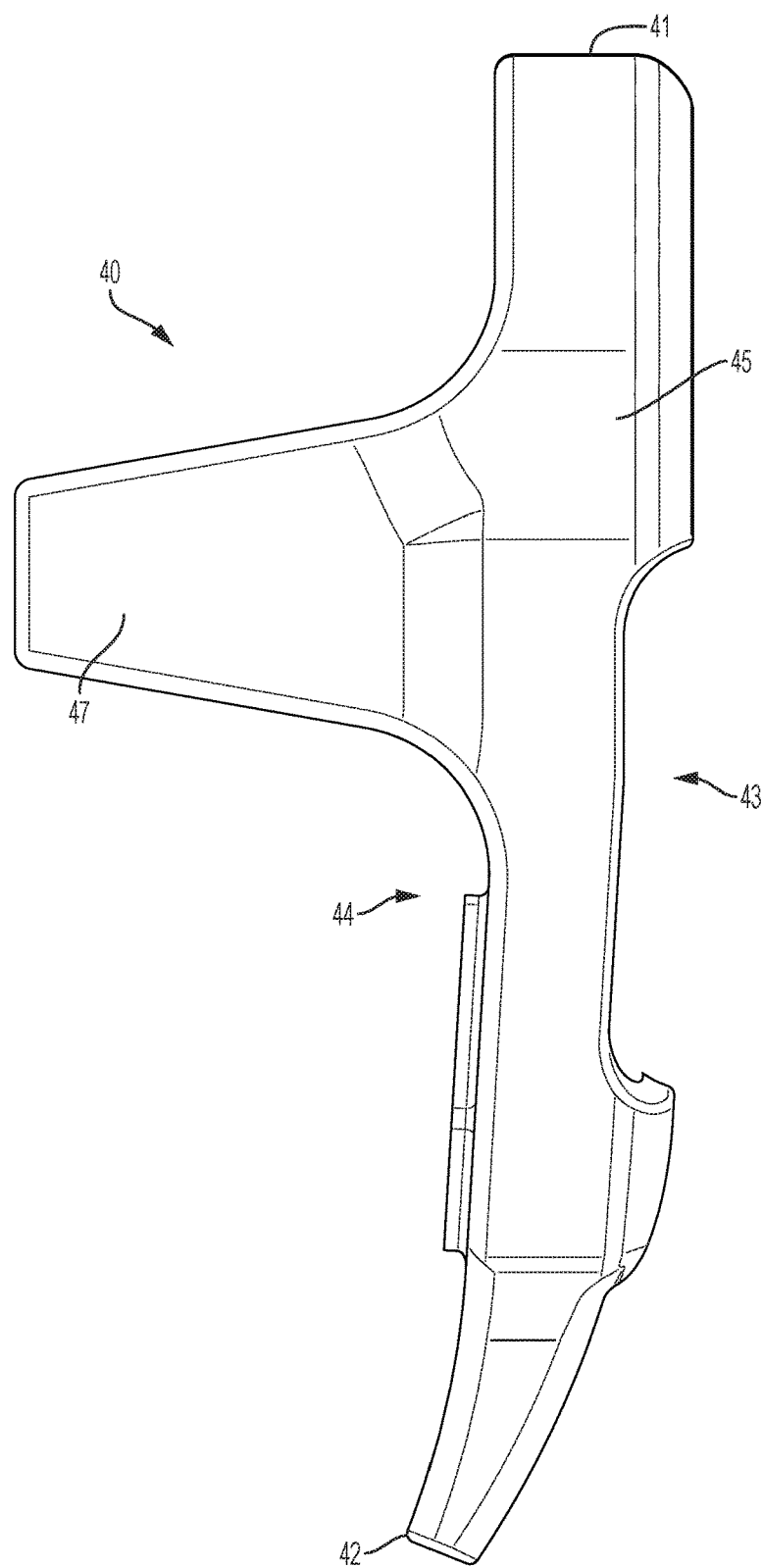
FIG. 12 is a left side elevation view of dual light tooth cup with tooth cup circuit board.
Figure 13:
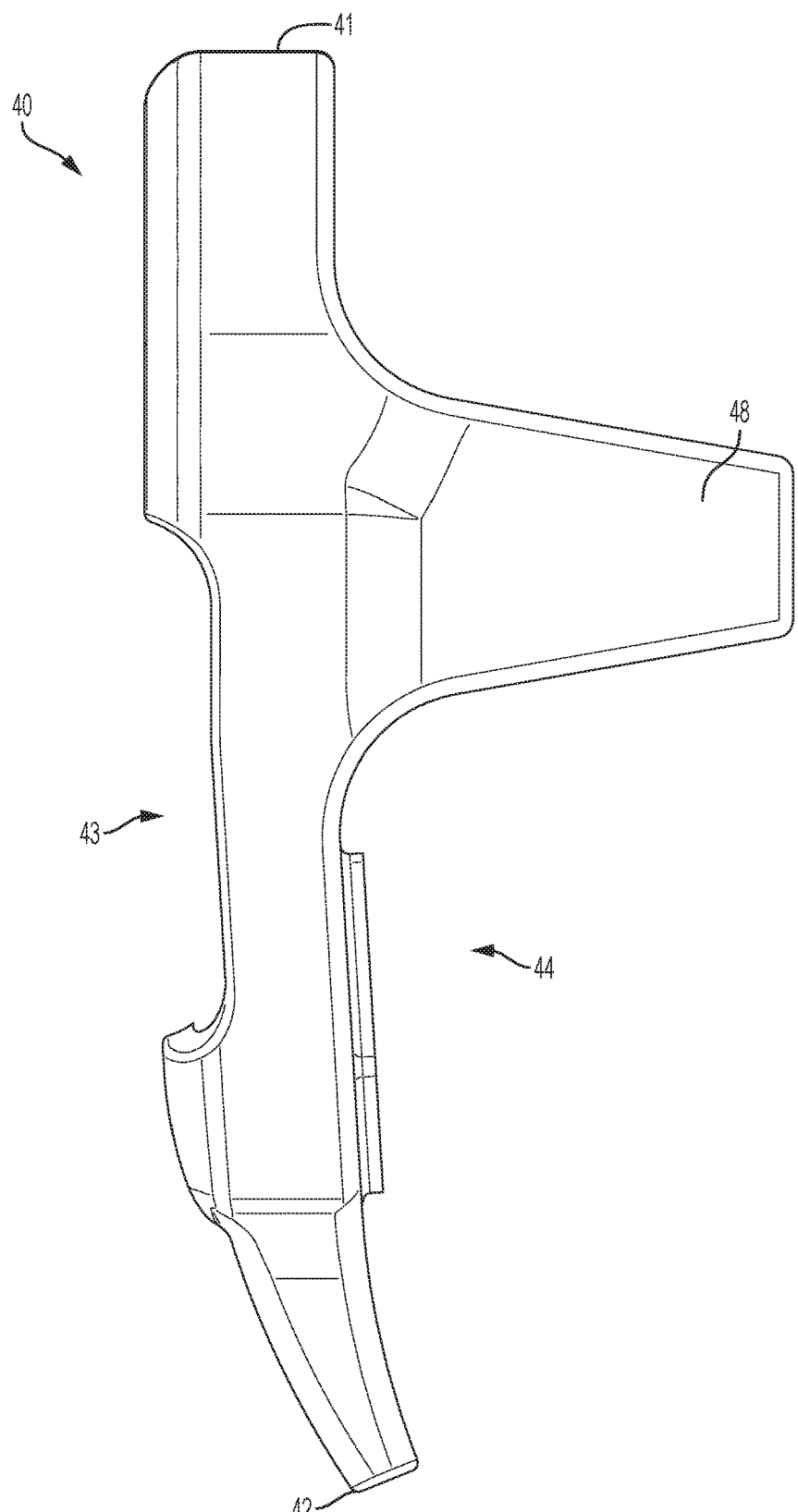
FIG. 13 is a right side elevation view of dual light tooth cup with tooth cup circuit board.
Figure 14:
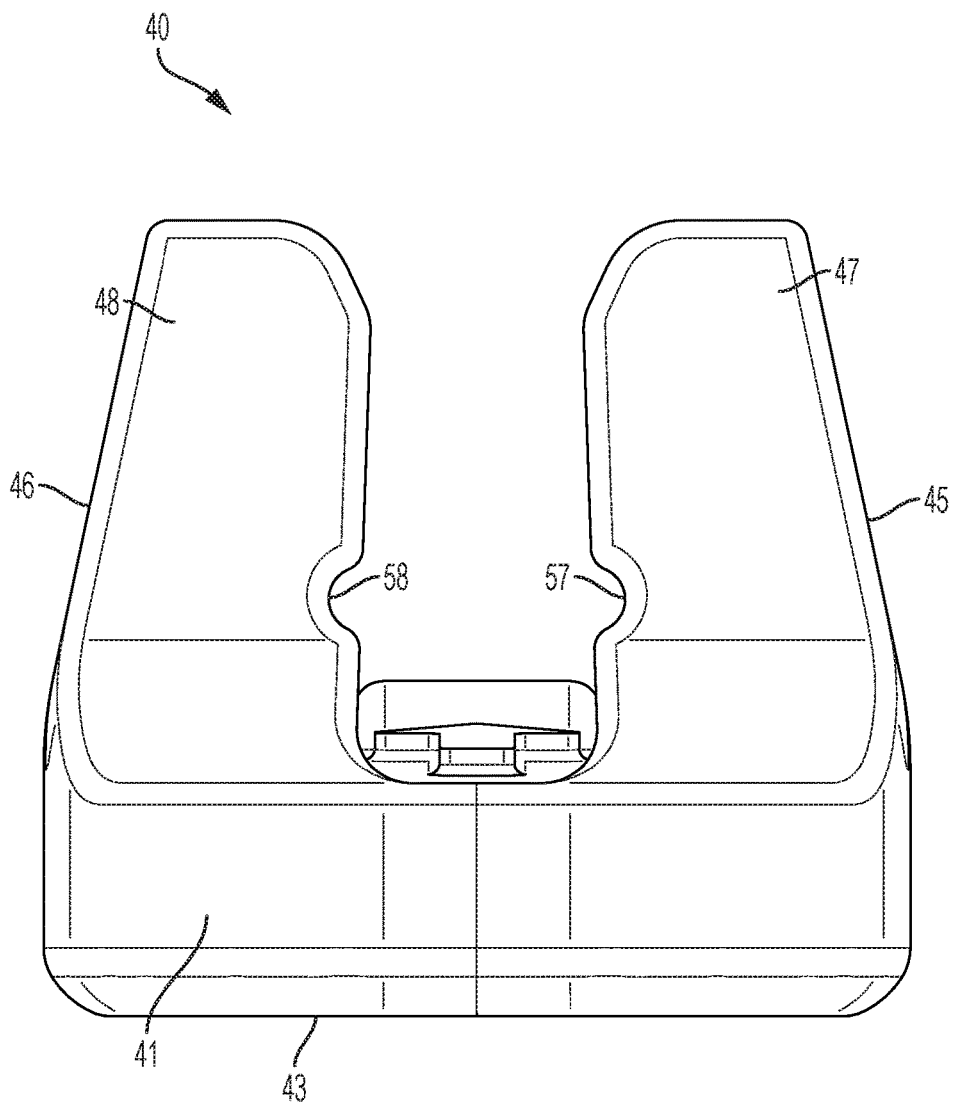
FIG. 14 is a top plan view of dual light tooth cup with tooth cup circuit board.
Figure 15:
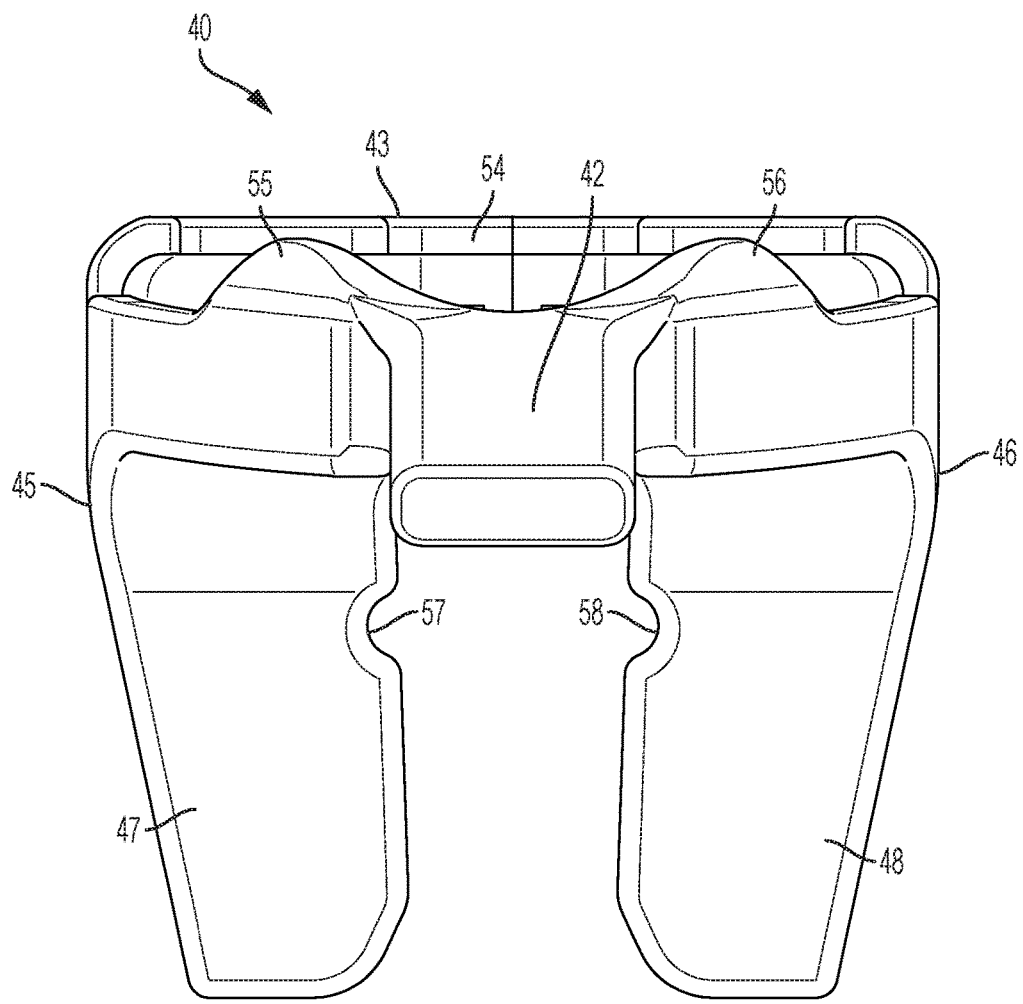
FIG. 15 is a bottom plan view of dual light tooth cup with tooth cup circuit board.
Figure 16:
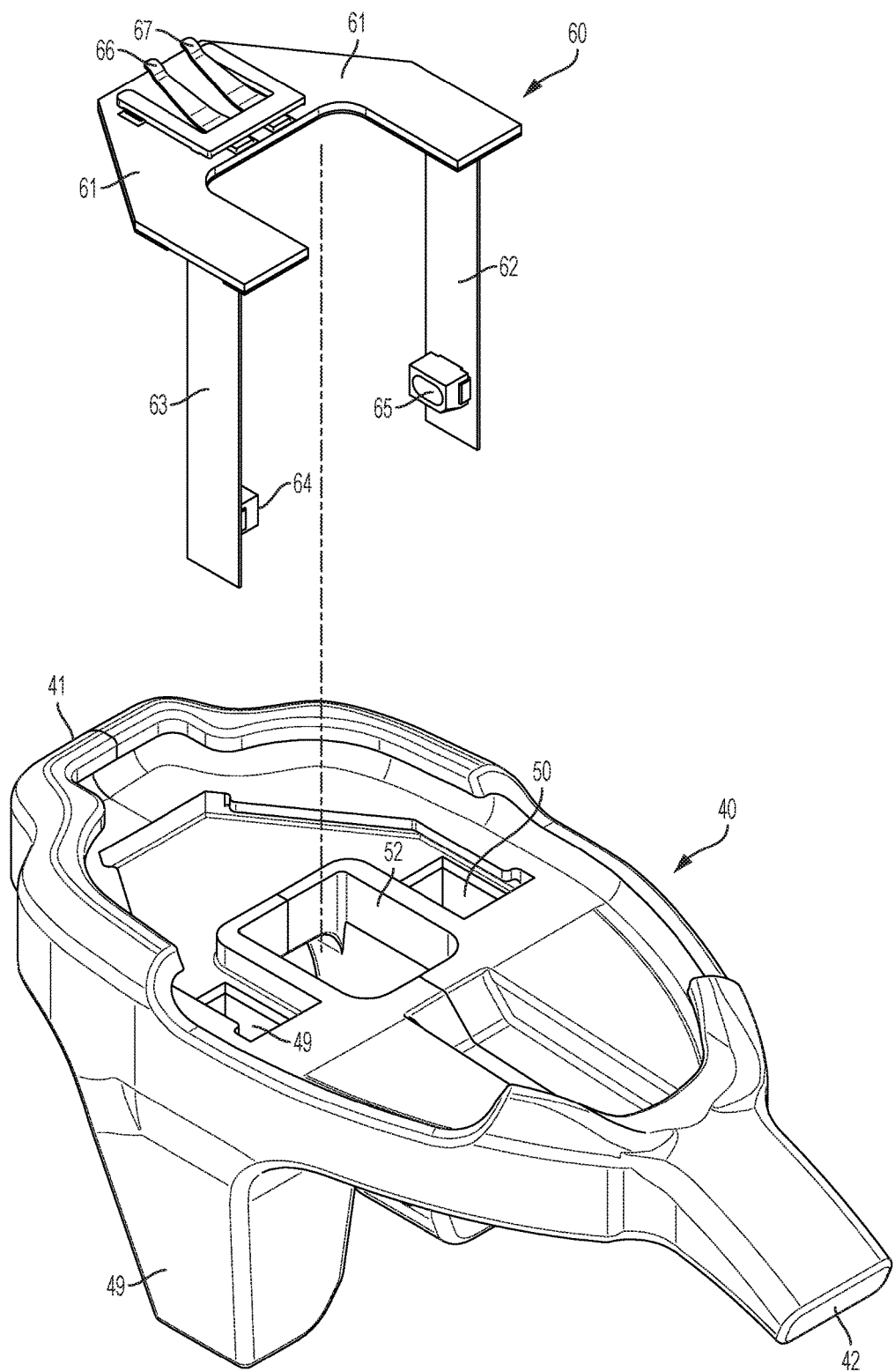
FIG. 16 is a perspective exploded view of dual light tooth cup with tooth cup circuit board depicting how tooth cup circuit board is inserted or fitted inside of dual light tooth cup.
Figure 17:
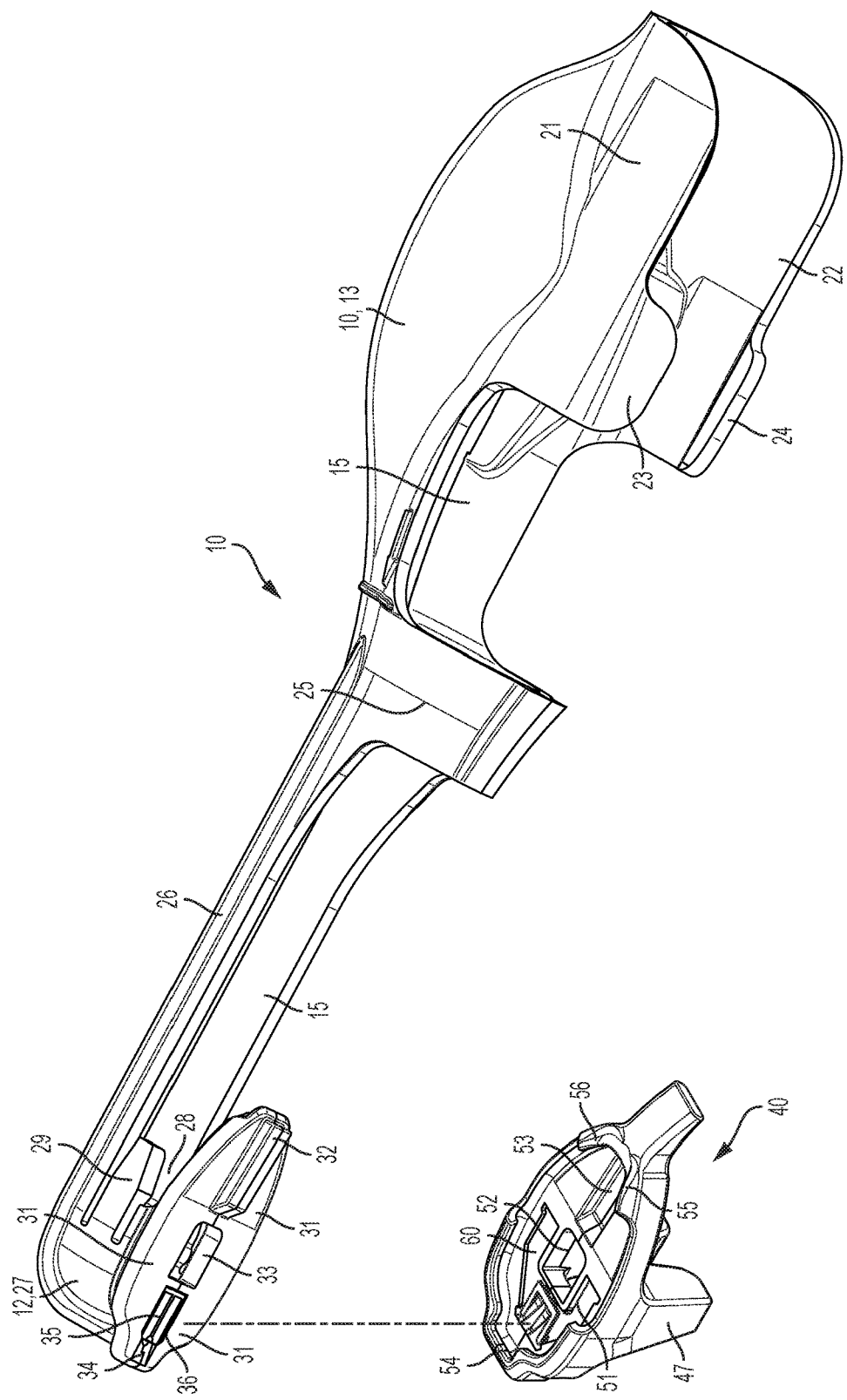
FIG. 17 is a perspective exploded view bilateral illumination attachment for dental camera depicting how dual light tooth cup is reversibly attached to the tooth cup slide ledge on the body of bilateral illumination attachment for dental camera.
Figure 18:
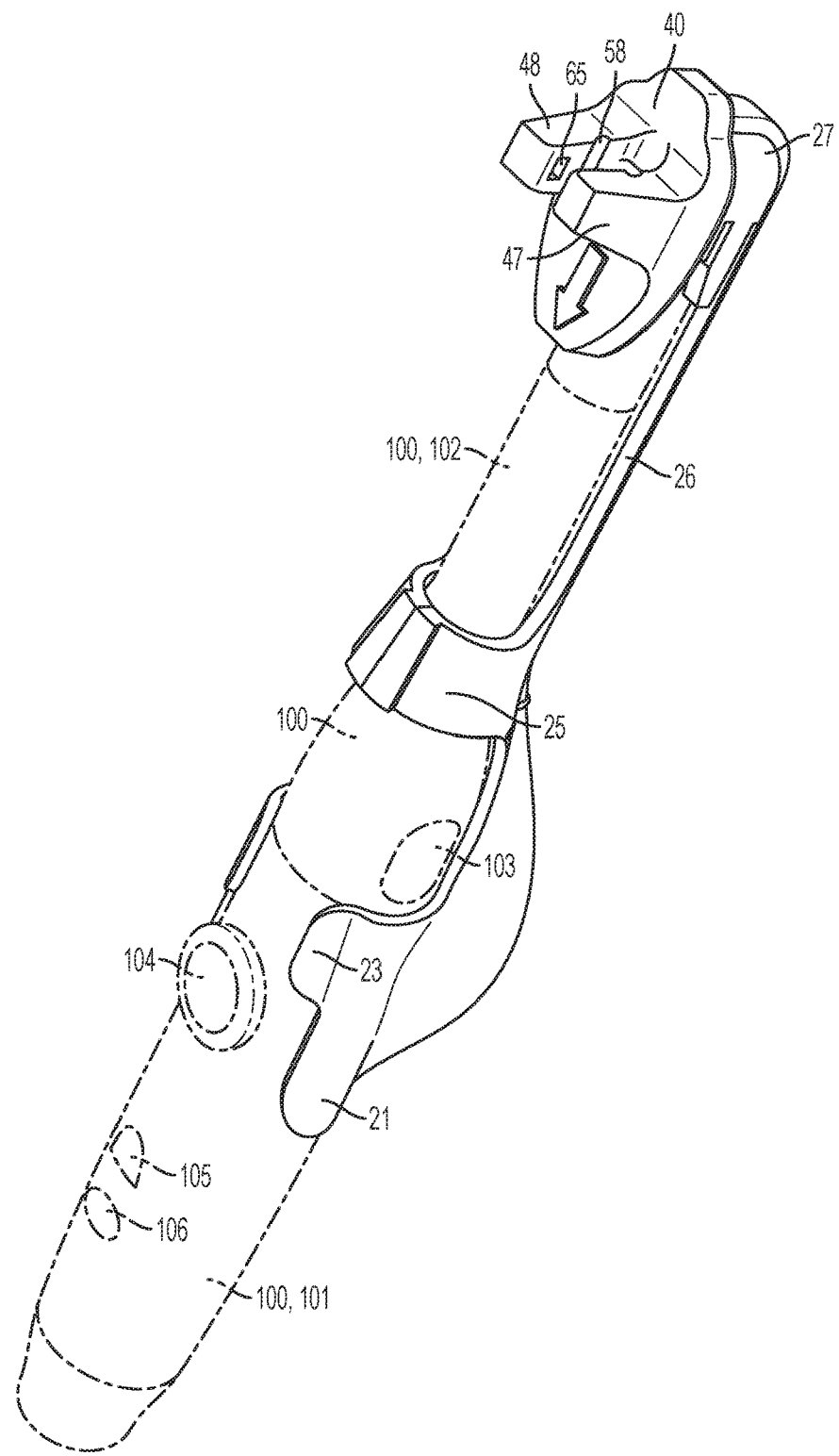
FIG. 18 is a front perspective view of bilateral illumination attachment for dental camera reversibly attached to a dental camera.
Figure 19:
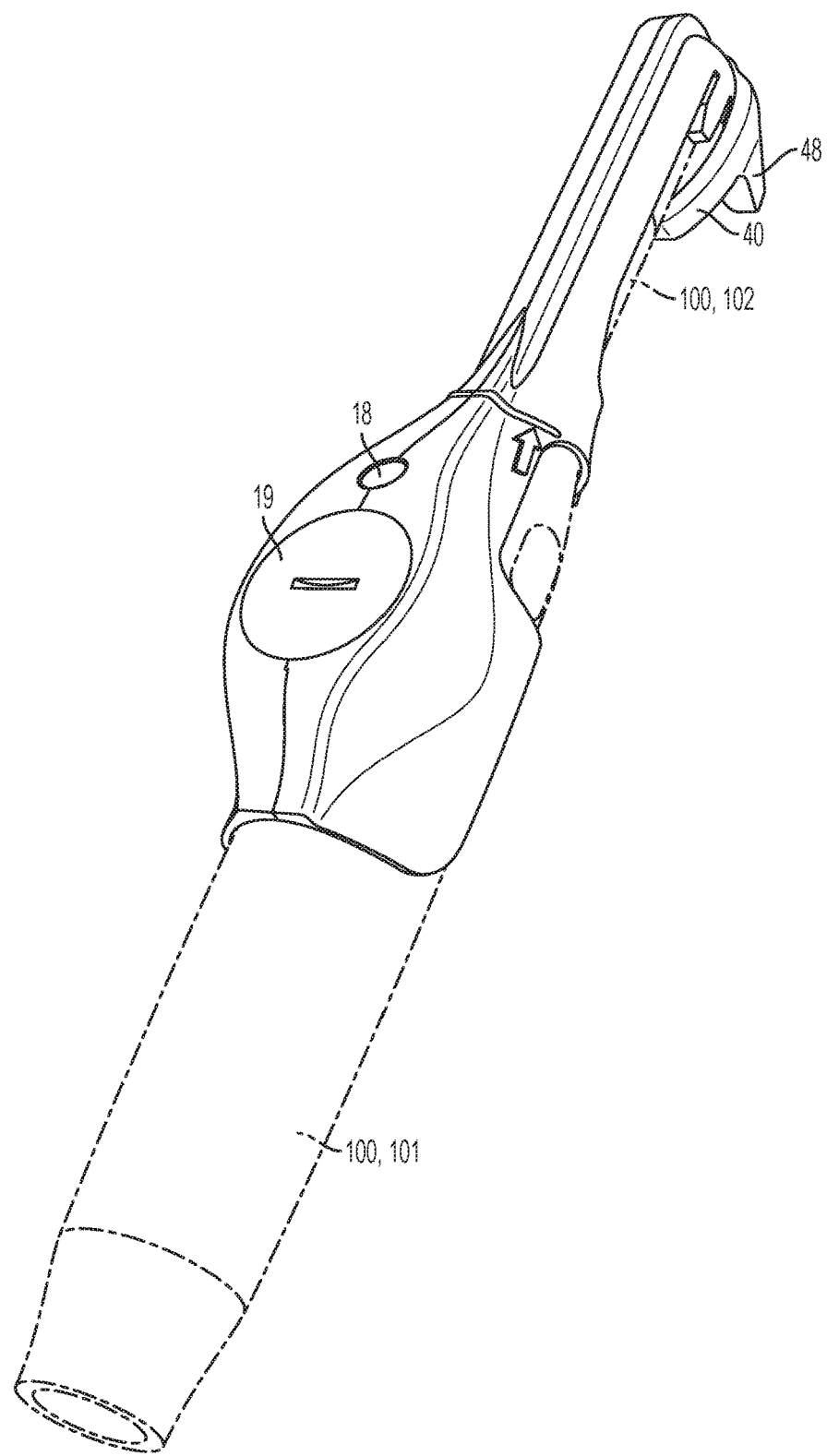
FIG. 19 is a rear front perspective view of bilateral illumination attachment for dental camera reversibly attached to a dental camera.

| DEFINITION LIST | |
|---|---|
| Term | Definition |
| 5 | Bilateral Illumination Attachment for Dental Camera |
| 10 | Body |
| 11 | Distal End of Body |
| 12 | Proximal End of Body |
| 13 | Left Side of Body |
| 14 | Right Side of Body |
| 15 | Concave Side of Body |
| 16 | Convex Side of Body |
| 17 | Mid-Line of Body |
| 18 | On Off Switch |
| 19 | Battery Compartment Lid |

-continued

DEFINITION LIST

| Term | Definition |
| --- | --- |
| 20 | Half Socket |
| 21 | Left Wing |
| 22 | Right Wing |
| 23 | Left Wing Tip |
| 24 | Right Wing Tip |
| 25 | Locating Collar |
| 26 | Gooseneck |
| 27 | Head |
| 28 | Concave Surface |
| 29 | Left Camera Clip |
| 30 | Right Camera Clip |
| 31 | Tooth Cup Slide Ledge |
| 32 | Key Ridge |
| 33 | Camera Port in Tooth Cup Slide Ledge |
| 34 | Wiring Port in Tooth Cup Slide Ledge |
| 35 | First Gooseneck Electrical Wire |
| 36 | Second Gooseneck Electrical Wire |
| 40 | Dual Light Tooth Cup |
| 41 | Distal End of Dual Light Tooth Cup |
| 42 | Proximal End of Dual Light Tooth Cup |
| 43 | Camera Side of Dual Light Tooth Cup |
| 44 | Tooth Side of Dual Light Tooth Cup |
| 45 | Left Side of Tooth Dual Light Cup |
| 46 | Right Side of Tooth Dual Light Cup |
| 47 | Left Arm |
| 48 | Right Arm |
| 49 | Left Arm Socket |
| 50 | Right Arm Socket |
| 51 | Circuit Board Recess |
| 52 | Camera Port in Tooth Cup |
| 53 | Key Notch |
| 54 | Distal Skirt |
| 55 | Left Proximal Skirt |
| 56 | Right Proximal Skirt |
| 57 | Left Crown Line |
| 58 | Right Crown Line |
| 60 | Tooth Cup Circuit Board |
| 61 | Base of Tooth Cup Circuit Board |
| 62 | Left Extension of Tooth Cup Circuit Board |
| 63 | Right Extension of Tooth Cup Circuit Board |
| 64 | Left Light Source |
| 65 | Right Light Source |
| 66 | First Electrical Contact |
| 67 | Second Electrical Contact |
| 100 | Dental Camera |
| 101 | Larger Diameter End or Proximal End of Dental Camera |
| 102 | Smaller Diameter End or Distal End of Dental Camera |
| 103 | Capture Switch on Dental Camera |
| 104 | Focus Wheel on Dental Camera |
| 105 | Light On Off Switch on Dental Camera |
| 106 | On Off Power Switch on Dental Camera |

DETAILED DESCRIPTION OF THE INVENTION

Bilateral illumination attachment for dental camera 5 is reversibly attachable to a dental camera 100. A dental camera 100 is a camera that is used to take pictures or images of the interior of a patient's mouth and the exterior of a patient's face. Dental cameras 100 are typically used to take a picture or capture an image of a problem tooth in order to show the patient and for record keeping purposes. A dental camera 100 is also known as an intraoral camera. All dental cameras 100 have a tapered cylindrical exterior shape with a larger diameter end 101 and a smaller diameter end 102 as depicted. The larger diameter end 101 is the gripping end where the operator grips or holds this end to operate the dental camera 100. The larger diameter end 101 of dental camera 100 is the proximal end of dental camera 100. The smaller diameter end 102 of dental camera 100 is the distal end of dental camera 100. The smaller diameter end 102 of dental camera 100 has a distal tip with an image sensor and a light source located thereon. The distal tip with image sensor and light source is placed into the interior of the patient's mouth when using bilateral illumination attachment for dental camera 5 to take pictures or images of the interior of a patient's mouth. There is a smooth taper between the larger diameter end 101 and the smaller diameter end 102 on the exterior surface of dental camera 100. Dental camera 100 has a capture switch 103, which is the button used to take pictures or capture images of a tooth. Dental camera 100 has a focus wheel 104, which is focus adjustment used to focus pictures or images of a tooth. Dental camera 100 has a light on off switch 105, which is the button used to control the flash or light on dental camera 100. Dental camera 100 has an on off power switch 106, which is the button turn the dental camera 100 on and off. There are many different brands of dental camera 100 in the market place where each brand may have its own specific tapered cylindrical shape, however, most, if not all, brands have a larger diameter end 101 with a smooth tapered mid-section leading to a smaller diameter end 102 as described above. Bilateral illumination attachment for dental camera 5 is reversibly attachable to any brand of dental camera 100 with a larger diameter end 101 and smooth tapered mid-section leading to a smaller diameter end 102. Since the exact dimensions of the larger diameter end 101 of different brand of dental cameras 100 may differ, a specifically sized sub-enamel illumination attachment for dental camera 5 may be required for each specific brand of dental camera 100.

Bilateral illumination attachment for dental camera 5 comprises: a body 10, a main circuit board, a battery, a dual light tooth cup 40, and a tooth cup circuit board 60. Body 10 is a specially shaped structural member that makes a slip-fit, press-fit, or snap-fit over the exterior surface of a dental camera 100. Body 10 is sterilizeable by heat or chemical means. Body 10 may be made from any known material that is rigid and capable of being sterilized by heat or chemical means. Body 10 may be made from steel, metal, composite, plastic, polymer, carbon fiber, fiberglass, epoxy, or similar. In best mode, as depicted, body 10 is a two-piece hollow clamshell structure. As depicted, there is a longitudinal seam running completely around body 10 defining the two pieces. In the hollow clamshell structure, there are two pieces or halves that press together and rigidly attach together like a clamshell. The hollow clamshell design makes for easier product assembly where first gooseneck electrical wire 35, second gooseneck electrical wire 36, main circuit board, and battery are installed in between the two hollow clamshell pieces prior to pressing them together or rigidly attaching them together to form body 10. The two pieces or halves may be rigidly attached together by any known means such as glue, adhesive, epoxy, welding, sonic welding, soldering, press-fit, clips, or similar.

Body 10 is a rigid oblong structural member with a distal end 11, a proximal end 12, a left side 13, a right side 14, a concave side 15, a convex side 16, and a longitudinal axis. Distal end 11 is the end of body 10 that is furthest from the operator during operation of bilateral illumination attachment for dental camera 5. Proximal end 12 is the end of body 10 that is closest to the operator during operation of bilateral illumination attachment for dental camera 5. Concave side 15 has a general concave shape and a concave surface. Concave side 15 is the side of body 10 that is faces or is adjacent to dental camera 100 when bilateral illumination attachment for dental camera 5 is properly attached to dental camera 100. Convex side 16 has a general convex shape and a convex surface. Convex side 16 is the side of body 10 that is opposite of dental camera 100 when bilateral illumination attachment for dental camera 5 is attached to dental camera 100. An on off switch 18 and a battery compartment lid 19 are located on convex side 16. Left side 13 is located on the operator's left side when facing the convex side 16. Right side 14 is located on the operator's right side when facing the convex side 16. There is a mid-line 17 the convex side 16 of body 10 located about halfway between distal end 11 and proximal end 12. Mid-line 17 divides body 10 longitudinally to yield a distal half and a proximal half. Mid-line 17 is a marking or visible line running across the surface of convex side 16. Mid-line 17 is a visible line running perpendicular to the longitudinal axis of body 10. Mid-line 17 is used during the disinfecting process as described below.

Convex side 16 comprises an electronics compartment. Electronics compartment is a hollow compartment or void area underneath the convex surface of convex side 16 directly beneath on off switch 18 and beneath battery compartment lid 19. Electronics compartment, on off switch 18, and battery compartment lid 19 are located on the proximal half of body 10 in between the proximal end 12 and the mid-line 17 of body 10. Electronics compartment functions to house a main circuit board and a battery. Main circuit board is a circuit board or motherboard comprising: a plurality of electrical circuits, a plurality of electrical contacts, and an on off switch 18. Electrical circuits include an integrated circuit or chip with read only memory and random access memory. Structurally, main circuit board is a rigid planar member with an upper surface and a lower surface. The upper surface faces convex side 16 and the lower surface faces concave side 15. On off switch 18 is attached to or soldered to the upper surface of main circuit board and thus has electrical continuity therewith. A portion of on off switch 18 protrudes through convex side 16 in order to provide operator access thereto. Main circuit board is larger than battery and extends from on off switch 18 to battery compartment lid 19. Battery is installed or placed onto the upper surface of main circuit board directly below battery compartment lid 19. Electrical contacts on main circuit board make electrical contact or continuity with the battery when the battery is installed. Battery is installed and replaced in the typical way that batteries are installed and replaced. Battery may be any known type of battery. In best mode, battery is a button type battery. Battery compartment lid 19 is reversibly attachable to the convex side 16 or body 10. Battery compartment lid 19 functions to retain battery within electronics compartment. Battery compartment lid 19 is removed to replace battery. Any known reversibly attachment means may be used such as: fastener, screw, clip, magnet, press-fit, threads, toggle, latch, or similar. In best mode, threads are used where battery compartment lid 19 is threaded onto the convex side 16 of body 10.

Concave side 15 is specially sized and shaped to make a slip-fit, press-fit, or snap-fit onto the exterior surface of a dental camera 100. A portion of this special shape is half socket 20. Concave side 15 comprises a half socket 20. Half socket 20 is located on the proximal half of body 10 in between the proximal end 12 and the mid-line 17 of body 10. Half socket 20 creates part of the general concave shape of concave side 15. Half socket 20 makes a snap-fit over the larger diameter end 101 of dental camera 100. Half socket 20 is a rigid hollow partial cylindrical member that is a "half-pipe" shape. Half socket 20 is a half pipe. Half socket has an inner diameter, an outer diameter, a distal end, a proximal end, and a longitudinal axis. The inner diameter of half socket 20 is sized to make a snap-fit over the outer diameter of the larger diameter end 101 of dental camera 100. Rigid hollow partial cylindrical member is partial because a portion of the side of the hollow cylindrical member is void or removed to yield an open space. A portion of the side of the hollow cylindrical member is void or open. Both ends of rigid hollow partial cylindrical member are void or open. These voids allow for easier insertion, attachment, detachment, and removal of the bilateral illumination attachment for dental camera 5 onto the dental camera 100.

Half socket 20 comprises: a left wing 21, a right wing 22, a left wing tip 23, and a right wing tip 24. Left wing 21 and left wing tip 23 are located on the operator's left side when facing the convex side 16. Right wing 22 and right wing tip 24 are located on the operator's right side when facing the convex side 16. Left wing 21 and left wing tip 23 comprise the left half of the rigid hollow partial cylindrical member. Left wing 21 is rigid arced member or curved member with an inner diameter, outer diameter, a distal end, a proximal end, a first side, and a second side. The inside diameter of left wing 21 is sized to make a snap-fit over the larger diameter end 101 of dental camera 100. Left wing 21 is the wider portion or base portion of the rigid hollow partial cylindrical member on the left side. The first side of left wing 21 is contiguous with left side 13. The second side of left wing 21 is contiguous with left wing tip 23. Left wing tip 23 is the more narrow portion or tip portion of the rigid hollow partial cylindrical member on the left side. Left wing tip 23 is rigid arced member or curved member with an inner diameter, outer diameter, a distal end, a proximal end, a first side, and a second side. The inside diameter of left wing tip 23 is sized to make a snap-fit over the larger diameter end 101 of dental camera 100. The first side of left wing tip 23 is contiguous with the second side of left wing 21. The second side of left wing tip 23 is adjacent to the void section of the rigid hollow partial cylindrical member. The length of left wing tip 23 is about 25-75 percent of that of left wing 21. The width of left wing tip 23 is less than that of left wing 21. Right wing 22 and right wing tip 24 comprise the right half of the rigid hollow partial cylindrical member. Right wing 22 is rigid arced member or curved member with an inner diameter, outer diameter, a distal end, a proximal end, a first side, and a second side. The inside diameter of right wing 22 is sized to make a snap-fit over the larger diameter end 101 of dental camera 100. Right wing 22 is the wider portion or base portion of the rigid hollow partial cylindrical member on the right side. The first side of right wing 22 is contiguous with right side 14. The second side of right wing 22 is contiguous with right wing tip 24. Right wing tip 24 is the more narrow portion or tip portion of the rigid hollow partial cylindrical member on the right side. Right wing tip 24 is rigid arced member or curved member with an inner diameter, outer diameter, a distal end, a proximal end, a first side, and a second side. The inside diameter of right wing tip 24 is sized to make a snap-fit over the larger diameter end 101 of dental camera 100. The first side of right wing tip 24 is contiguous with the second side of right wing 22. The second side of right wing tip 24 is adjacent to the void section of the rigid hollow partial cylindrical member. The length of right wing tip 24 is about 25-75 percent of that of right wing 22. The width of right wing tip 24 is about 25-50 percent of that of right wing 22. Wings 21,22 and wing tips 23,24 function to wrap-around the larger diameter end 101 of dental camera 100 and reversible attach thereto by press-fit or slip-fit. The void section between the second side of left wing tip 23 and the second side of right wing tip 24 functions to allow clearance space for the distal end or smaller diameter end 102 of dental cameral to be passed there through during attachment and detachment of bilateral illumination attachment for dental camera 5. This clearance space makes it much easier to attach and detach bilateral illumination attachment for dental camera 5 to dental camera 100. An alternate description of half socket 20 is that left wing 21, left wing tip 23, right wing 22, and right wing tip 24 collectively form a half pipe shape. The inner diameter of this half pipe is sized to make a snap-fit over the outer diameter of the larger diameter end 101 of dental camera 100. Left wing 21 forms left half of the wider base of the half pipe shape. Right wing 22 forms right half of the wider base of the half pipe shape. Left wing tip 23 forms the narrower tip or end of the half pipe shape on the left. Right wing tip 24 forms the narrower tip or end of the half pipe shape on the right. The half pipe shape spans about 190 to 330 degrees of a complete 360-degree circle or full pipe. Left wing 21 spans about 90 to 130 degrees of a complete circle. Left wing tip 23 spans about 5 to 30 degrees of a complete circle. Right wing 22 spans about 90 to 130 degrees of a complete circle. Right wing tip 24 spans about 5 to 30 degrees of a complete circle. The void section at the top of the half pipe functions to allow clearance space for the distal end or smaller diameter end 102 of dental cameral to be passed there through during attachment and detachment of bilateral illumination attachment for dental camera 5. This clearance space makes it much easier to attach and detach bilateral illumination attachment for dental camera 5 to dental camera 100.

Concave side 15 further comprises a locating collar 25. Locating collar 25 is located on the distal half of body 10 in between the distal end 11 and the mid-line 17 of body 10. Locating collar 25 is adjacent to the mid-line 17 of body 10. Locating collar 25 is a rigid tapered cylindrical member with open ends. Locating collar 25 has a distal end, a proximal end, a tapered side, and a longitudinal axis. Distal end has a circular opening with an inner diameter. Proximal end has a circular opening with an inner diameter. The inner diameter of distal end is smaller than that of proximal end. Tapered side is tapered with a smooth tapered inner diameter that varies linearly from distal end to proximal end to yield a smooth taper. The inner diameter of tapered side is sized and shaped to make a slip-fit or press-fit over the tapered outer diameter of dental camera 100. The longitudinal axis of locating collar 25 is parallel with that of body 10. The proximal end of locating collar 25 is contiguous with or rigidly attached to the distal end of half socket 20. The longitudinal axis of locating collar 25 is coincident with that of half socket 20.

Body 10 further comprises a gooseneck 26. Gooseneck 26 is an elongated rigid structural member. Gooseneck 26 has a distal end, proximal end, left side, right side, concave side, convex side, a length, and a longitudinal axis. The proximal end of gooseneck 26 is adjacent to and contiguous with or rigidly attached the distal end of locating collar 25. Left side is located on the operator's left side when facing the convex side. Right side is located on the operator's right side when facing the convex side. Concave side of gooseneck 26 is a partial cylindrical surface with an inner diameter. The inner diameter of concave side is sized and shaped to make a slip-fit or press-fit over the outer diameter of the smaller diameter end 102 of dental camera 100. The inner diameter of concave side is equivalent to that of the distal end of locating collar 25 thereby making a smooth transition of inner diameter between the locating collar 25 and the gooseneck 26. Concave side of gooseneck 26 is a partial cylindrical surface because most of the side of the hollow cylindrical member is void or removed to yield an open space. When bilateral illumination attachment for dental camera is attached to dental camera 100, concave side of gooseneck 26 covers about 90-180 degrees of the outer diameter of the smaller diameter end 102 of dental camera 100 when attached thereto. Both ends of rigid hollow partial cylindrical member are void or open. The voids on the side and ends allow for easier insertion, attachment, detachment, and removal of the bilateral illumination attachment for dental camera 5 onto the dental camera 100. The length of gooseneck 26 is about 75-95 percent of the length of the distal half of body 10. The longitudinal axis of gooseneck 26 is parallel with that of body 10. The longitudinal axis of gooseneck 26 is parallel with that of locating collar 25. The interior of gooseneck 26 has a longitudinal wire conduit running along the entire length of gooseneck 26. Longitudinal wire conduit is an internal channel or cavity running from the electronics compartment to a wiring port 34 in a tooth cup slide ledge 31. Longitudinal wire conduit has a distal end and a proximal end. The proximal end of longitudinal wire conduit connects with electronics compartment. The distal end of longitudinal wire conduit connects with wiring port 34 on tooth cup slide ledge 31. Longitudinal wire conduit is a conduit for a first gooseneck electrical wire 35 and a second gooseneck electrical wire 36.

Body 10 further comprises a first gooseneck electrical wire 35 and second gooseneck electrical wire 36. First and second gooseneck electrical wires 35,36 are each an electrical wire or metallic wire capable of transmitting electrical signals there through. First and second gooseneck electrical wires 35,36 each have a distal end, a proximal end, and a longitudinal axis. The proximal end of first gooseneck electrical wire 35 has electrical continuity with an electrical contact on main circuit board. The proximal end of second gooseneck electrical wire 36 has electrical continuity with an electrical contact on main circuit board. The distal end of electrical wire 35 extends to wiring port 34 in tooth cup slide ledge 31. The distal end of second gooseneck electrical wire 36 extends to wiring port 34 in tooth cup slide ledge 31. First gooseneck electrical wire 35 and second gooseneck electrical wire 36 each extend longitudinally across the full length of gooseneck 26 from the mid-section of half socket 20 to the mid-section area of tooth cup slide ledge 31. First gooseneck electrical wire 35 and second gooseneck electrical wire 36 are sterilizeable by heat or chemical means. First gooseneck electrical wire 35 and second gooseneck electrical wire 36 may be made from any known material that is capable of carrying and electrical signal. First gooseneck electrical wire 35 and second gooseneck electrical wire 36 may be made from copper, steel, metal, composite, plastic, polymer, carbon fiber, or similar.

Body 10 further comprises a head 27. Head 27 is a specially shaped rigid structural member that functions as the point of attachment and detachment for the distal tip of dental camera 100. Head 27 is reversibly attachable over the distal tip of dental camera 100. Head 27 is rigid cup-shaped, socket-shaped, or U-shaped member where the cup, socket, or U shape is reversibly attachable over the distal tip of dental camera 100. Head 27 has a distal end and a proximal end. The distal end of head 27 is the closed end or bottom of the cup, socket, or U shape. The proximal end of head 27 is the open end or top of the cup, socket, or U shape. The distal end of gooseneck 26 is contiguous with or rigidly attached a point on the proximal end of head 27. Note that the longitudinal wire conduit passes through the entire cup-shape, socket-shape, or U-shape of head 27 and into tooth cup slide ledge 31.

With cup-shaped and socket-shaped modes of head 27, the cup and socket shapes are defined by a concave surface 28, a left camera clip 29, a right camera clip 30, and a tooth cup slide ledge 31 on head 27. Concave surface 28 is a radiused surface with an inner diameter that is sized and shape to make a slip-fit, press-fit, or snap-fit with the exterior surface of the smaller diameter end 102 or distal end of dental camera 100. Concave surface 28 is located opposite from tooth cup slide ledge 31 on the cup or socket shape. Right camera clip 30 is located on the operator's right side when facing the convex side 16 of body 10. Left camera clip 29 is located on the operator's left side when facing the convex side 16 of body 10. Left camera clip 29 is located on the opposite side of the cup or socket shape from right camera clip 30. The distal end of gooseneck is contiguous with or rigidly attached to concave surface 28. Left camera clip 29 is a clip, hinged clip member, or detent member that clips onto a protrusion located on the smaller diameter end 102 or distal end of most dental cameras 100. Left camera clip 29 may alternately be a pin without a clip. Alternately, left camera clip 29 may be a pin, pillar, or guidepost that does not clip or latch onto the smaller diameter end 102 or distal end of dental camera 100. Right camera clip 30 is a clip, hinged clip member, or detent member that clips onto a protrusion located on the smaller diameter end 102 or distal end of most dental camera 100. Right camera clip 30 may alternately be a pin without a clip. Alternately, right camera clip 30 may be a pin, pillar, or guidepost that does not clip or latch onto the smaller diameter end 102 or distal end of dental camera 100.

With the U-shaped mode of head 27, the U-shape is defined by the concave surface 28 and the tooth cup slide ledge 31 on head 27. With the U-shaped mode of head 27, there is no left camera clip 29 and there is not right camera clip 30. The concave surface 28 and tooth cup slide ledge 31 from a U-shape.

Tooth cup slide ledge 31 is a rigid planar member. Tooth cup slide ledge 31 has a distal end, a proximal end, a camera side, and a tooth side. Distal end is the end of tooth cup slide ledge 31 that is furthest from the operator during operation of bilateral illumination attachment for dental camera 5. Proximal end is the end of tooth cup slide ledge 31 that is closest to the operator during operation of bilateral illumination attachment for dental camera 5. The distal end of tooth cup slide ledge 31 is contiguous with or rigidly attached a point on the proximal end of head 27. The camera side faces or is adjacent to dental camera 100 when bilateral illumination attachment for dental camera 5 is attached to dental camera 100. Camera side of tooth cup slide ledge 31 is sized and shaped to make a slip-fit or press-fit with outer surface of the image sensor and the outer surface of the light on the distal end of dental camera 100. The tooth side of tooth cup slide ledge 31 faces or is adjacent to the patient's tooth during use of the bilateral illumination attachment for dental camera 5. Tooth cup slide ledge 31 is the point of reversible slideable attachment and detachment for one or more dual light tooth cups 40. A plurality of dual light tooth cups 40 are reversibly attachable to the tooth side of tooth cup slide ledge 31.

Tooth cup slide ledge 31 comprises: a key ridge 32, a camera port 33, and a wiring port 34. Key ridge 32 is a rigid protrusion projecting upwards or outwards perpendicularly from the tooth side of tooth cup slide ledge 31. Rigid protrusion may be of any particular shape. Key ridge 32 functions to help located a dual light tooth cup 40 properly onto tooth cup slide ledge 31 when attaching the dual light tooth cup 40 to tooth cup slide ledge 31. Key ridge mates with a key notch 53 on a dual light tooth cup 40 described below. Camera port 33 is an open space, void, or aperture in tooth cup slide ledge 31 to allow for the image sensor on the distal end of dental camera 100 to have an open path or clear field of view of the tooth during use of the bilateral illumination attachment for dental camera 5 for sub-enamel illumination or bilateral illumination of the tooth. An open path or clear field of view between the image sensor and the tooth is required to allow the image sensor on dental camera 100 to capture an image or take a picture of the tooth during sub-enamel illumination or bilateral illumination of the tooth. Wiring port 34 is a port or access opening at the distal end of longitudinal wire conduit. The distal end of first gooseneck electrical wire 35 extends through wiring port 34 and overhangs, overlaps, or is folded over the tooth side of tooth cup slide ledge 31. The distal end of second gooseneck electrical wire 36 extends through wiring port 34 and overhangs overlaps, or is folded over the tooth side of tooth cup slide ledge 31. Thus the distal ends of first and second gooseneck electrical wires 35,36 lay on the camera side of tooth cup slide ledge 31. The distal ends of first and second gooseneck electrical wires 35,36 are rigidly attached to tooth cup slide ledge 31 in this position. Rigid attachment may be accomplished by any known means such as glue, adhesive, epoxy, welding, sonic welding, soldering, press-fit, or similar. As described below, the distal ends of first and second gooseneck electrical wires 35,36 make contact or electrical continuity with first and second electrical contacts 66,67 on a tooth cup circuit board 60 when a dual light tooth cup is properly attached to tooth cup slide ledge 31.

In order to reversibly attach bilateral illumination attachment for dental camera 5 to a dental camera 100, the smaller diameter end 102 and the distal tip of dental camera 100 are inserted through the void section between left and right wing tips 23,24 and pushed towards the distal end 11 of body 10. Then, the smaller diameter end 102 and the distal tip of dental camera 100 are inserted through the locating collar 25 from its proximal end. Then, the smaller diameter end 102 and the distal tip of dental camera 100 are inserted into cup or socket shape of head 27 on order to snap into place. The snap signals a proper press-fit or slip-fit of bilateral illumination attachment for dental camera 5 to dental camera 100. The press-fit or slip-fit is reversible. Bilateral illumination attachment for dental camera 5 is removed from dental camera 100 by pulling dental camera 100 proximally and/or pressing body 10 distally until body 10 snaps off of dental camera 100.

Dual light tooth cup 40 is inserted into a patient's mouth during use of the bilateral illumination attachment for dental camera 5. Dual light tooth cup 40 is placed over the coronal surface or crown of the tooth of interest where a left light source 64 and a right light source 65 straddle the tooth of interest and project light directly towards each other, into the interior of the tooth of interest in order to effect or yield sub-enamel illumination or bilateral illumination of the tooth of interest so that the image sensor on the distal tip of dental camera 100 may then take or capture an image or picture from the light projected out of the coronal surface or crown of the tooth of interest.

Dual light tooth cup 40 comprises a base, a left arm 47, and a right arm 48. Dual light tooth cup 40 is a semi-rigid, flexible, elastic, or resilient structural member that houses or retains a tooth cup circuit board 60 with left and right light sources 64,65. Dual light tooth cup 40 has a distal end 41, a proximal end 42, a camera side 43, a tooth side 44, a left side 45, and a right side 46. Distal end 41 is the end of dual light tooth cup 40 that is furthest from the operator during operation of bilateral illumination attachment for dental camera 5. Proximal end 42 is the end of dual light tooth cup 40 that is closest to the operator during operation of bilateral illumination attachment for dental camera 5. Camera side 43 faces or is adjacent to dental camera 100 when bilateral illumination attachment for dental camera 5 is attached to dental camera 100. Tooth side 44 faces or is adjacent to the patient's tooth during use of the bilateral illumination attachment for dental camera 5. Left side 45 is located on the operator's left side when facing the camera side 43 of dual light tooth cup 40. Right side 46 is located on the operator's right side when facing the camera side 43 of dual light tooth cup 40. Base is a semi-rigid, flexible, elastic, or resilient planar member. One side of base is the camera side 43 and the other side of base is the tooth side 44. Dual light tooth cup 40 may be made from steel, metal, composite, plastic, polymer, carbon fiber, fiberglass, epoxy, or similar.

The camera side 43 of dual light tooth cup 40 has a circuit board recess 51. Circuit board recess 51 is a recess or gully in the camera side 43 of dual light tooth cup 40. Circuit board recess 51 is located near the distal end 41 of dual light tooth cup 40. Circuit board recess 51 is the inverse shape of tooth cup circuit board 60 so that tooth cup circuit board 60 may be inserted therein. There is a left arm socket 49 on the left side of circuit board recess 51. Left arm socket 49 is an internal channel or cavity running from the camera side 43 of dual light tooth cup 40, through a left arm 47, to exit laterally from the tooth end of left arm 47. There is a right arm socket 50 on the right side of circuit board recess 51. Right arm socket 50 is an internal channel or cavity running from the camera side 43 of dual light tooth cup 40, through a right arm 48, to exit laterally from the tooth end of right arm 48.

The camera side 43 of dual light tooth cup 40 also has a camera port 52. Camera port 52 is an open space, void, or aperture through the base of dual light tooth cup 40. Camera port 52 on dual light tooth cup 40 aligns with camera port 33 on tooth cup slide ledge 31 when dual light tooth cup 40 is properly attached to tooth cup slide ledge 31. Camera port 52 functions to allow to allow for the image sensor on the distal end of dental camera 100 to have an open path or clear field of view of the tooth during use of the bilateral illumination attachment for dental camera 5 for sub-enamel illumination or bilateral illumination of the tooth. An open path or clear field of view between the image sensor and the tooth is required to allow the image sensor on dental camera 100 to capture an image or take a picture of the tooth during sub-enamel illumination or bilateral illumination of the tooth. Camera port 52 appears on the tooth side 44 of dual light tooth cup 40.

The camera side 43 of dual light tooth cup 40 also has a key notch 53. Key notch 53 and key ridge 32 function to help align and properly locate dual light tooth cup 40 onto the tooth cup slide ledge 31 on body 10 when attaching dual light tooth cup 40 to bilateral illumination attachment for dental camera 5. Key notch 53 is a rigid protrusion extending perpendicularly out of the camera side 43 of dual light tooth cup 40. Key notch 53 is the inverse shape of key ridge 32 on tooth cup slide ledge 31. Key ridge 32 and key notch 53 are sized and shaped to make a slip-fit or press-fit within each other. Any particular shape for key ridge 32 and/or key notch 53 may be used. In best mode, as depicted, key ridge is rectangular cuboid shaped and key notch 53 is inverse rectangular cuboid shaped.

The tooth side 44 of dual light tooth cup 40 has a left arm 47 protruding upwards or outwards therefrom. Left arm 47 is a semi-rigid, flexible, elastic, or resilient oblong structural member that houses or retains a left extension 62 on a tooth cup circuit board 60. Left extension 62 is a portion of tooth cup circuit board 60 as described below. Left arm 47 is a semi-rigid, flexible, elastic, or resilient hollow oblong protrusion extending outwards from tooth side 44. Left arm 47 has a camera end that is located adjacent to dental camera 100 when bilateral illumination attachment for dental camera 5 is properly attached to dental camera 100. Left arm 47 has a tooth end that is located adjacent to patient's tooth when bilateral illumination attachment for dental camera 5 is in use. Left arm has four sides. Left arm 47 has a longitudinal axis that is perpendicular to the plane of tooth side 44 and the plane of the base of dual light tooth cup 40. The longitudinal axis of left arm 47 is concentric with left arm socket 49 on the camera side 43. The hollow interior of left arm 47 is left arm socket 49. Left arm socket 49 is a longitudinal cavity, void, or conduit running along the longitudinal axis or length of left arm 47. Left arm socket 49 has a camera end that is located adjacent to dental camera 100 when bilateral illumination attachment for dental camera 5 is properly attached to dental camera 100. Camera end of left arm socket 49 extends to the circuit board recess 51 on the camera side 43. Left arm socket 49 has a tooth end that is located adjacent to patient's tooth when bilateral illumination attachment for dental camera 5 is in use. The tooth end of left arm socket 49 extends to a lateral exit on the tooth end of left arm 47. Left arm 47 houses or retains left extension 62 and left light source 64. Left arm 47 may optionally have a left crown line 57 on one of its sides. Left crown line 57 is a visible line or marking on the left arm 47 that is used to align with the crown of the target tooth in order to properly position and locate left light source 64 onto the target tooth to properly effectuate sub-enamel illumination or bilateral illumination of the target tooth.

The tooth side 44 of dual light tooth cup 40 has a right arm 48 protruding upwards or outwards therefrom. Right arm 48 is a semi-rigid, flexible, elastic, or resilient oblong structural member that houses or retains a right extension 63 on a tooth cup circuit board 60. Right extension 63 is a portion of tooth cup circuit board 60 as described below. Right arm 48 is a semi-rigid, flexible, elastic, or resilient hollow oblong protrusion extending outwards from tooth side 44. Right arm 48 has a camera end that is located adjacent to dental camera 100 when bilateral illumination attachment for dental camera 5 is properly attached to dental camera 100. Right arm 48 has a tooth end that is located adjacent to patient's tooth when bilateral illumination attachment for dental camera 5 is in use. Right arm 48 has four sides. Right arm 48 has a longitudinal axis that is perpendicular to the plane of tooth side 44 and the plane of the base of dual light tooth cup 40. The longitudinal axis of right arm 48 is concentric with right arm socket 50 on the camera side 43. The hollow interior of right arm 48 is right arm socket 50. Right arm socket 50 is a longitudinal cavity, void, or conduit running along the longitudinal axis or length of left arm 47. Right arm socket 50 has a camera end that is located adjacent to dental camera 100 when bilateral illumination attachment for dental camera 5 is properly attached to dental camera 100. Camera end of right arm socket 50 extends to the circuit board recess 51 on the camera side 43. Right arm socket 50 has a tooth end that is located adjacent to patient's tooth when bilateral illumination attachment for dental camera 5 is in use. The tooth end of right arm socket 50 extends to a lateral exit on the tooth end of right arm 48. Right arm 48 houses or retains right extension 63 and right light source 65. Right arm 48 may optionally have a right crown line 58 on one of its sides. Right crown line 58 is a visible line or marking on the right arm 48 that is used to align with the crown of the target tooth in order to properly position and locate right light source 65 onto the target tooth to properly effectuate sub-enamel illumination or bilateral illumination of the target tooth.

Tooth cup circuit board 60 is housed or retained within dual light tooth cup 40. Tooth cup circuit board 60 is a circuit board comprising: a plurality of electrical circuits and a plurality of electrical contacts. Tooth cup circuit board 60 further comprises: a base 61, a left extension 62, a right extension 63, a left light source 64, a right light source 65, a first electrical contact 66, and a second electrical contact 67.

Base 61 is a planar member with a plurality of electrical circuits and a plurality of electrical contacts thereon. Base 61 has a distal end, a proximal end, a camera side, a tooth side, a left side, and a right side. Distal end is the end of base 61 that is furthest from the operator during operation of bilateral illumination attachment for dental camera 5. Proximal end is the end of base 61 that is closest to the operator during operation of bilateral illumination attachment for dental camera 5. Camera side faces or is adjacent to dental camera 100 when bilateral illumination attachment for dental camera 5 is attached to dental camera 100. Tooth side faces or is adjacent to the patient's tooth during use of the bilateral illumination attachment for dental camera 5. Left side is located on the operator's left side when facing the convex side 16 of body 10. Right side is located on the operator's right side when facing the convex side 16 of body 10.

Left extension 62 is an oblong planar member with a plurality of electrical circuits and a plurality of electrical contacts thereon. Left extension 62 has a distal end, a proximal end, a left side, a right side, and a longitudinal axis. Distal end is the end of left extension 62 that is furthest from the operator during operation of bilateral illumination attachment for dental camera 5. Proximal end is the end of left extension 62 that is closest to the operator during operation of bilateral illumination attachment for dental camera 5. Left side of left extension 62 is located on the operator's left side when facing the convex side 16 of body 10. Right side of left extension 62 is located on the operator's right side when facing the convex side 16 of body 10. Left extension 62 has a length of about 0.2-2.0 inches and a width of about 0.05-0.5 inches.

Right extension 63 is an oblong planar member with a plurality of electrical circuits and a plurality of electrical contacts thereon. Right extension 63 has a distal end, a proximal end, a left side, a right side, and a longitudinal axis. Distal end is the end of right extension 63 that is furthest from the operator during operation of bilateral illumination attachment for dental camera 5. Proximal end is the end of right extension 63 that is closest to the operator during operation of bilateral illumination attachment for dental camera 5. Left side of right extension 63 is located on the operator's left side when facing the convex side 16 of body 10. Right side of right extension 63 is located on the operator's right side when facing the convex side 16 of body 10. Right extension 63 has a length of about 0.2-2.0 inches and a width of about 0.05-0.5 inches. In best mode, as depicted, left and right extensions 62,63 are identical in size.

The proximal end of left extension 62 is contiguous with or rigidly attached to the tooth side of base 61 on the left side of base 61 with the longitudinal axis of left extension 62 perpendicular to the plane of base 61 so that left extension 62 protrudes perpendicularly outward from the distal side of base 61. Left extension 62 functions to structurally hold left light source 64 in the proper position to effectuate bilateral illumination or bilateral illumination of a tooth. The proximal end of left extension 62 has electrical continuity with base 61. Left extension 62 also functions to electrically connect left light source 64 to base 61. Left light source 64 is rigidly attached to the right side of left extension 62 on the distal end of left extension 62. Left light source 64 has electrical continuity with left extension 62.

The proximal end of right extension 63 is contiguous with or rigidly attached to the tooth side of base 61 on the right side of base 61 with the longitudinal axis of right extension 63 perpendicular to the plane of base 61 so that right extension 63 protrudes perpendicularly outward from the distal side of base 61. Right extension 63 functions to structurally hold right light source 65 in the proper position to effectuate sub-enamel illumination or bilateral illumination of a tooth. The proximal end of right extension 63 has electrical continuity with base 61. Right extension 63 also functions to electrically connect right light source 65 to base 61. Right light source 65 is rigidly attached to the left side of right extension 63 on the distal end of right extension 63. Right light source 65 has electrical continuity with right extension 63. Left and right light sources 64,65 have electrical continuity with each other.

Left light source 64 and right light source 65 face each other directly. Left light source 64 shines directly towards right light source 65 and vice versa. Left light source 64 and right light source 65 are coincident with each other. Left and right light sources 64,65 must be in alignment and directly face each other in order to properly effectuate sub-enamel illumination or bilateral illumination of a tooth. Left and right light sources 64,65 are each an electrical light source. Any known type and/or color of electrical light source may be used such as incandescent, fluorescent, halogen, CFL, LED, or similar. In best mode, left and right light sources 64,65 are each white LED lights.

First electrical contact 66 is located on the camera side of base 61 on the distal end of base 61. A second electrical contact 67 is also located on the camera side of base 61 on the distal end of base 61. First electrical contact 66 is located on the left side of second electrical contacts 67. First and second electrical contacts 66,67 are each electrical contacts that have electrical continuity with base 61. First electrical contact 66 has electrical continuity with left light source 64. Second electrical contact 67 has electrical continuity with right light source 65. First and second electrical contacts 66,67 function to make electrical continuity with first and second gooseneck electrical wires 35,36 respectively when dual light tooth cup 40 is properly attached to tooth cup slide ledge 31 of body 10. When dual light tooth cup 40 is properly attached to tooth cup slide ledge 31 of body 10 there is electrical continuity between motherboard and left light source 64 and electrical continuity between motherboard and right light source 65.

A plurality of dual light tooth cups 40 are reversibly slideably attachable to tooth cup slide ledge 31. A dual light tooth cup 40 is retained onto tooth cup slide ledge 31 by a proximal skirt 54, a left distal skirt 55, and a right distal skirt 56 on dual light tooth cup 40. The camera side 43 of dual light tooth cup 40 has a proximal skirt 54, a left distal skirt 55, and a right distal skirt 56. Proximal skirt 54, a left distal skirt 55, and a right distal skirt 56 each function to help retain dual light tooth cup 40 onto tooth cup slide ledge 31 when attached thereto. Proximal skirt 54, a left distal skirt 55, and a right distal skirt 56 are each a flexible, elastic, or resilient skirt member, flange member, or clamp member on the edge of dual light tooth cup 40. Proximal skirt 54, a left distal skirt 55, and a right distal skirt 56 each wrap around an edge of tooth cup slide ledge 31 the grip and hold the edge of tooth cup slide ledge 31. In best mode, proximal skirt 54, a left distal skirt 55, and a right distal skirt 56 are each flange members with a "C" cross-section.

In order to attach a dual light tooth cup 40 to tooth cup slide ledge 31, the proximal end 42 of the camera side 43 of dual light tooth cup 40 is slid onto the distal end of the tooth side of tooth cup slide ledge 31 until left and right distal skirts 55,56 each snap onto or clamp around the proximal end of the tooth side of tooth cup slide ledge 31. As this happens, the distal skirt 55 should snap onto or clamp around the distal end of the tooth side of tooth cup slide ledge 31. The arrow depicted on the tooth side 44 of dual light tooth cup 40 depicts the direction in which a dual light tooth cup 40 is properly slid onto or attached onto tooth cup slide ledge 31. To remove a dual light tooth cup 40 from tooth cup slide ledge 31, the dual light tooth cup 40 is pushed or slid in the distal direction while holding body 10 still in order to remove proximal skirt 54, left distal skirt 55, and right distal skirt 56 from their clamping positions around the edges of tooth cup slide ledge 31. Since proximal skirt 54, left distal skirt 55, and right distal skirt 56 are flexible, elastic, or resilient this can be accomplished. Once proximal skirt 54, left distal skirt 55, and right distal skirt 56 are released from the edges of tooth cup slide ledge 31, dual light tooth cup 40 may be pushed or slid distally to be removed from the tooth cup slide ledge 31 and body 10. To remove a dual light tooth cup 40 from tooth cup slide ledge 31, the dual light tooth cup 40 is pushed or slid in the direction opposite of the arrow depicted on the tooth side 44 of dual light tooth cup 40.

A dual light tooth cup 40 touches or makes contact with the inside of a patient's mouth during use of the bilateral illumination attachment for dental camera 5. Therefore each dual light tooth cups 40 must be sterilized or discarded after use with a particular patient. Since the dual light tooth cup 40 contains expensive electronics and a circuit board, a sterilizeable version of dual light tooth cup 40 is included. A dual light tooth cup 40 of this invention can be sterilized and used again with a new patent. Alternately, a dual light tooth cup 40 of this invention can be discarded where a new a dual light tooth cup 40 may be used for each new patient.

The head 27 or other portion of body 10 also touches or makes contact with the inside of a patient's mouth during use of the bilateral illumination attachment for dental camera 5. Therefore body 10 must be sterilized or discarded after use with a particular patient. The distal end 11 of body 10 can be sterilized and used again with a new patent. The distal end 11 of body 10 may be dipped or soaked in a sterilizing solution by inserting the distal end 11 of body 10 into the solution up to the mid-line 17 on body 10. Body 10 of bilateral illumination attachment for dental camera 5 is deigned to be soaked in sterilizing solution up to the mid-line 17. Thus, mid-line 17 of body 10 functions to indicate the level of sterilizing solution during sterilization.

What is claimed is:

1. A bilateral illumination attachment for dental camera comprising: a body; a main circuit board; a battery; a dual light tooth cup; and a tooth cup circuit board, wherein, said body is a rigid oblong structural member with a distal end, a distal half, a proximal end, a proximal half, a left side, a right side, a concave side, and a convex side,
said body is reversibly attachable to a dental camera,
said convex side of said body has a convex surface,
said convex side of said body has an electronics compartment therein,
said electronics compartment is a hollow compartment or void area underneath said convex surface of said body,
said concave side of said body has a concave surface,
said concave side of said body further comprises a half socket,
said half socket is a rigid hollow partial cylindrical member with open ends that is a "half-pipe" shape,
said half socket has an inner diameter, an outer diameter, a distal end, a proximal end, and a longitudinal axis,
said concave side of said body further comprises a locating collar,
said locating collar is a rigid tapered cylindrical member with open ends,
said locating collar has a distal end, a proximal end, a tapered side, and a longitudinal axis,
said proximal end of said locating collar is contiguous with or rigidly attached to said distal end of said half socket,
said longitudinal axis of said locating collar is coincident with said longitudinal axis of said half socket,
said body further comprises a gooseneck,
said gooseneck is an elongated rigid structural member with a distal end, a proximal end, a left side, a right side, a concave side, a convex side, a length, and a longitudinal axis,
said proximal end of said gooseneck is contiguous with or rigidly attached to said distal end of said locating collar,
said longitudinal axis of said gooseneck is parallel with said longitudinal axis of said locating collar,
said body further comprises a head,
said head is a rigid cup-shaped, socket-shaped, or U-shaped member with a distal end and a proximal end,
said distal end of said gooseneck is contiguous with or rigidly attached to said proximal end of said head,
said body further comprises a tooth cup slide ledge,
said tooth cup slide ledge is a rigid planar member with a distal end, a proximal end, a camera side, a tooth side,
said distal end of said tooth cup slide ledge is contiguous with or rigidly attached to said proximal end of said head,
said tooth cup slide ledge comprises a camera port and a wiring port,
said camera port is an open space, void, or aperture in said tooth cup slide ledge that is aligned with an image sensor on said dental camera when said body is attached to said dental camera,
said body further comprises a longitudinal wire conduit,
said longitudinal wire conduit is an internal channel or cavity running longitudinally across the entire length of said gooseneck, extending from said electronics compartment to said wiring port,
said wiring port is a port or access opening into a longitudinal wire conduit,
said body further comprises: a first gooseneck electrical wire and a second gooseneck electrical wire,
said first and second gooseneck electrical wires are each an electrical wire or metallic wire,
said first and second gooseneck electrical wires are each located in said longitudinal wire conduit,
said first and second gooseneck electrical wires each have a distal end and a proximal end,
said distal end of said first electrical wire is located on said tooth side of said tooth cup slide ledge,
said distal end of said second electrical wire is located on said tooth side of said tooth cup slide ledge, said proximal end of said first electrical wire is located in said electronics compartment, said proximal end of said second electrical wire is located in said electronics compartment, said main circuit board is a circuit board or motherboard with a plurality of electrical circuits and a plurality of electrical contacts, said main circuit board is located in said electronics compartment, said battery is a battery, said battery is located in said electronics compartment, said battery has electrical continuity with said main circuit board, said proximal end of said first gooseneck wire has electrical continuity with said main circuit board, said proximal end of said second gooseneck wire has electrical continuity with said main circuit board, said distal end of said first gooseneck electrical wire extends out of or protrudes from said wiring port, said distal end of said second gooseneck electrical wire extends out of or protrudes from said wiring port, said dual light tooth cup is a semi-rigid, flexible, elastic, or resilient structural member that houses or retains said tooth cup circuit board, said dual light tooth cup comprises a base, a left arm, and a right arm, wherein, said base is a planar member with a tooth side and a camera side, said left arm is an oblong structural member protruding perpendicularly from said tooth side of said base, said right arm is an oblong structural member protruding perpendicularly from said tooth side of said base, said tooth cup circuit board is a circuit board with a plurality of electrical circuits and a plurality of electrical contacts, said tooth cup circuit board comprises a left light source and a right light source, said tooth cup circuit board is housed or retained within said dual light tooth cup, said left light source is a light source that is housed or retained within said left arm, said right light source is a light source that is housed or retained within said right arm, said dual light tooth cup is reversibly slideably attachable to said tooth cup slide ledge on said body, said distal end of said first gooseneck wire has electrical continuity with said tooth cup circuit board when said dual light tooth cup is attached to said tooth cup slide ledge, and said distal end of said second gooseneck wire has electrical continuity with said tooth cup circuit board when said dual light tooth cup is attached to said tooth cup slide ledge.

2. A bilateral illumination attachment for dental camera as recited in claim 1 wherein said distal half of said body is sterilizeable.

3. A bilateral illumination attachment for dental camera as recited in claim 1 wherein said dual light tooth cup is sterilizeable.

4. A bilateral illumination attachment for dental camera as recited in claim 1 wherein a plurality of said dual light tooth cups are reversibly slideably attachable to said tooth cup slide ledge.

5. A bilateral illumination attachment for dental camera as recited in claim 4 wherein said distal half of said body is sterilizeable.

6. A bilateral illumination attachment for dental camera as recited in claim 4 wherein each of said plurality of said dual light tooth cups is sterilizeable.

\* \* \* \* \*